United States Patent
Wang et al.

(10) Patent No.: US 9,790,500 B2
(45) Date of Patent: Oct. 17, 2017

(54) DUAL TARGETING ANTISENSE OLIGONUCLEOTIDES AS APOPTOTIC INHIBTOR THERAPEUTIC COMPOSTIONS AND METHODS FOR THEIR USE IN THE TREATMENT OF CANCER

(71) Applicants: Yuzhuo Wang, Vancouver (CA); Hui Xue, Vancouver (CA); Sze Ue Luk, Vancouver (CA); Peter Wilhelm Gout, Vancouver (CA); Martin E. Gleave, Vancouver (CA); Colin C. Collins, Vancouver (CA)

(72) Inventors: Yuzhuo Wang, Vancouver (CA); Hui Xue, Vancouver (CA); Sze Ue Luk, Vancouver (CA); Peter Wilhelm Gout, Vancouver (CA); Martin E. Gleave, Vancouver (CA); Colin C. Collins, Vancouver (CA)

( * ) Notice: Subject to any disclaimer, the term of this patent is extended or adjusted under 35 U.S.C. 154(b) by 0 days.

(21) Appl. No.: 15/211,857

(22) Filed: Jul. 15, 2016

(65) Prior Publication Data

US 2017/0015997 A1    Jan. 19, 2017

Related U.S. Application Data

(60) Provisional application No. 62/193,568, filed on Jul. 16, 2015.

(51) Int. Cl.
```
C12N 15/11      (2006.01)
C12N 15/113     (2010.01)
A61K 31/7125    (2006.01)
```
(52) U.S. Cl.
CPC ........ *C12N 15/113* (2013.01); *A61K 31/7125* (2013.01); *C12N 2310/11* (2013.01); *C12N 2310/315* (2013.01); *C12N 2310/3125* (2013.01); *C12N 2310/3145* (2013.01); *C12N 2310/3181* (2013.01); *C12N 2310/3233* (2013.01); *C12N 2310/3341* (2013.01); *C12N 2310/3519* (2013.01); *C12N 2310/51* (2013.01)

(58) Field of Classification Search
None
See application file for complete search history.

(56) References Cited

PUBLICATIONS

De Almagro MC and Vucic D., "The inhibitor of apoptosis (IAP) proteins are critical regulators of signaling pathways and targets for anti-cancer therapy", Exp Oncol., 2012; 34(3):200-211.
Krajewska M., et al., "Elevated expression of inhibitor of apoptosis proteins in prostate cancer", Clin Cancer Res., 2003, 9(13):4914-4925.
Rodriguez L., et al., "Polypurine reverse Hoogsteen hairpins as a gene therapy tool against survivin in human prostate cancer PC3 cells in vitro and in vivo", Biochem Pharmacol., 2013, 86(11):1541-1554.
Bartke T., et al., "Dual role of BRUCE as an antiapoptotic IAP and a chimeric E2/E3 ubiquitin ligase", Mol Cell., 2004, 14(6):801-811.
Hao Y., et al., "Apollon ubiquitinates SMAC and caspase-9, and has an essential cytoprotection function", Nat Cell Biol., 2004, 6(9):849-860.
Qiu XB and Goldberg AL., "The membrane-associated inhibitor of apoptosis protein, BRUCE/Apollon, antagonizes both the precursor and mature forms of Smac and caspase-9", J Biol Chem., 2005, 280(1):174-182.
Chen Z., et al., "A human IAP-family gene, apollon, expressed in human brain cancer cells", Biochem Biophys Res Commun., 1999, 264(3):847-854.
Chu L., et al., "Oncolytic adenovirus-mediated shRNA against Apollon inhibits tumor cell growth and enhances antitumor effect of 5-fluorouracil", Gene Ther., 2008, 15(7):484-494.
Pohl C and Jentsch S., "Final stages of cytokinesis and midbody ring formation are controlled by BRUCE", Cell., 2008, 132(5):832-845.
Martin SJ. "An Apollon vista of death and destruction", Nat Cell Biol., 2004, 6(9):804-806.
Sung KW, et al., "Overexpression of Apollon, an antiapoptotic protein, is associated with poor prognosis in childhood de novo acute myeloid leukemia", Clin Cancer Res., 2007, 13(17):5109-5114.
Bianchini M., et al., "Comparative study of gene expression by cDNA microarray in human colorectal cancer tissues and normal mucosa", Int J Oncol., 2006, 29(1):83-94.
Sekine K., et al., "HtrA2 cleaves Apollon and induces cell death by IAP-binding motif in Apollon-deficient cells", Biochem Biophys Res Commun., 2005, 330(1):279-285.
Tassi E., et al., "Role of Apollon in human melanoma resistance to antitumor agents that activate the intrinsic or the extrinsic apoptosis pathways", Clin Cancer Res., 2012, 18(12):3316-3327.
Lamers F., et al., "Identification of BIRC6 as a novel intervention target for neuroblastoma therapy", BMC Cancer, 2012, 12:285.
Qiu XB, et al., "Nrdp1-mediated degradation of the gigantic IAP, BRUCE, is a novel pathway for triggering apoptosis", EMBO J., 2004, 23(4):800-810.
Dong X, et al. "Elevated expression of BIRC6 protein in non-small-cell lung cancers is associated with cancer recurrence and chemoresistance", J Thorac Oncol., 2013, 8(2):161-170.
Dias and Stein, "Antisense Oligonucleotides: Basic Concepts and Mechanisms", Molecular Cancer Therapeutics (2002) 1:347-355.
Southwell et al., "In Vivo Evaluation of Candidate Allele-specific Mutant Huntingtin Gene Silencing Antisense Oligonucleotides", Molecular Therapy (2014) 22(12):2093-2106.

(Continued)

*Primary Examiner* — Kate Poliakova-Georgantas
(74) *Attorney, Agent, or Firm* — Glenn J. Foulds; Bozicevic, Field & Francis LLP

(57) ABSTRACT

Provided herein are compositions, method and uses for modulating IAP activity or for the treatment of cancer. The compositions comprise dual-targeting antisense oligonucleotides (dASO) for administration to a cancer cell, wherein the cancer cell may be characterized by elevated expression of one or more of BIRC6, cIAP1 or survivin. The cancer may be selected from one or more of: prostate cancer; childhood de novo acute myeloid leukemia; colorectal cancer; neuroblastoma; melanoma; and non-small cell lung cancer. The prostate cancer may be castration-resistant prostate cancer (CRPC).

37 Claims, 27 Drawing Sheets

(56) References Cited

PUBLICATIONS

Murray et al., "TricycloDNA-modified oligo-2'-deoxyribonucleotides reduce scavenger receptor B1 mRNA in hepatic and extra-hepatic tissues—a comparative study of oligonucleotide length, design and chemistry", Nucleic Acids Research (2012).

Luk et al. "The BIRC6 gene as a novel target for therapy of prostate cancer: dual targeting of inhibitors of apoptosis", Oncotarget (2014) 5(16):2229-24912.

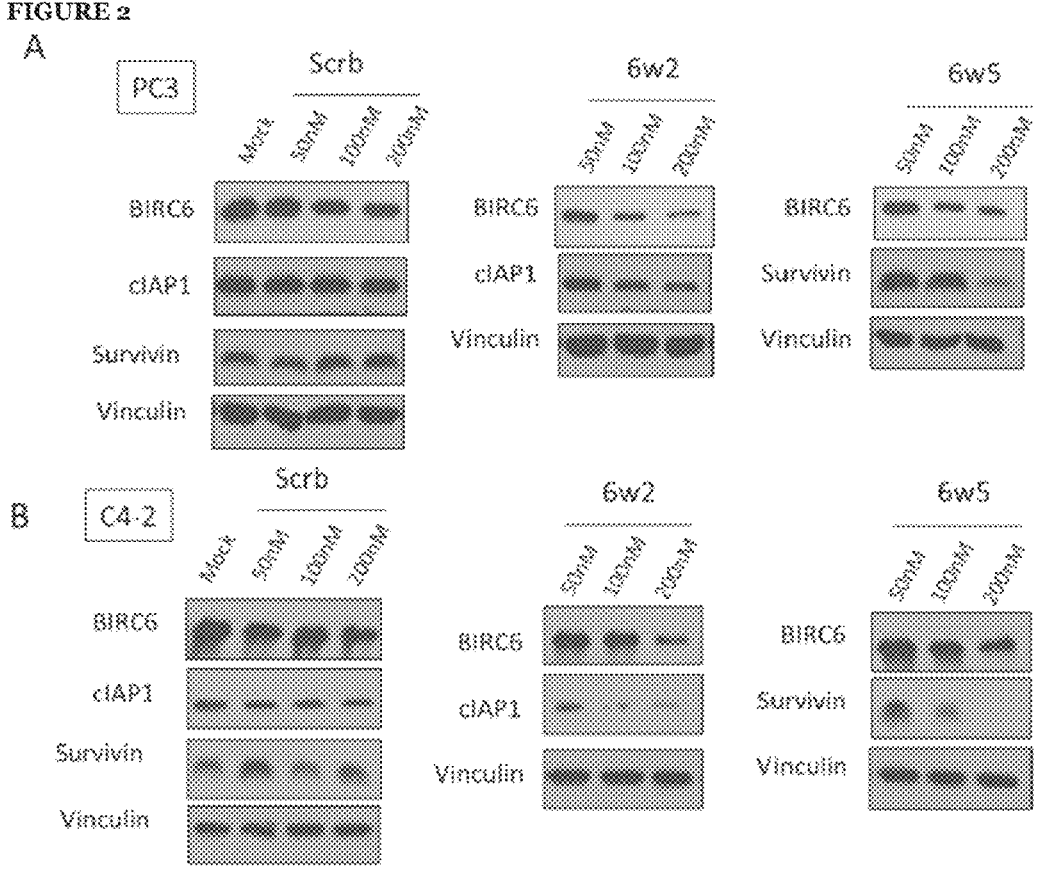

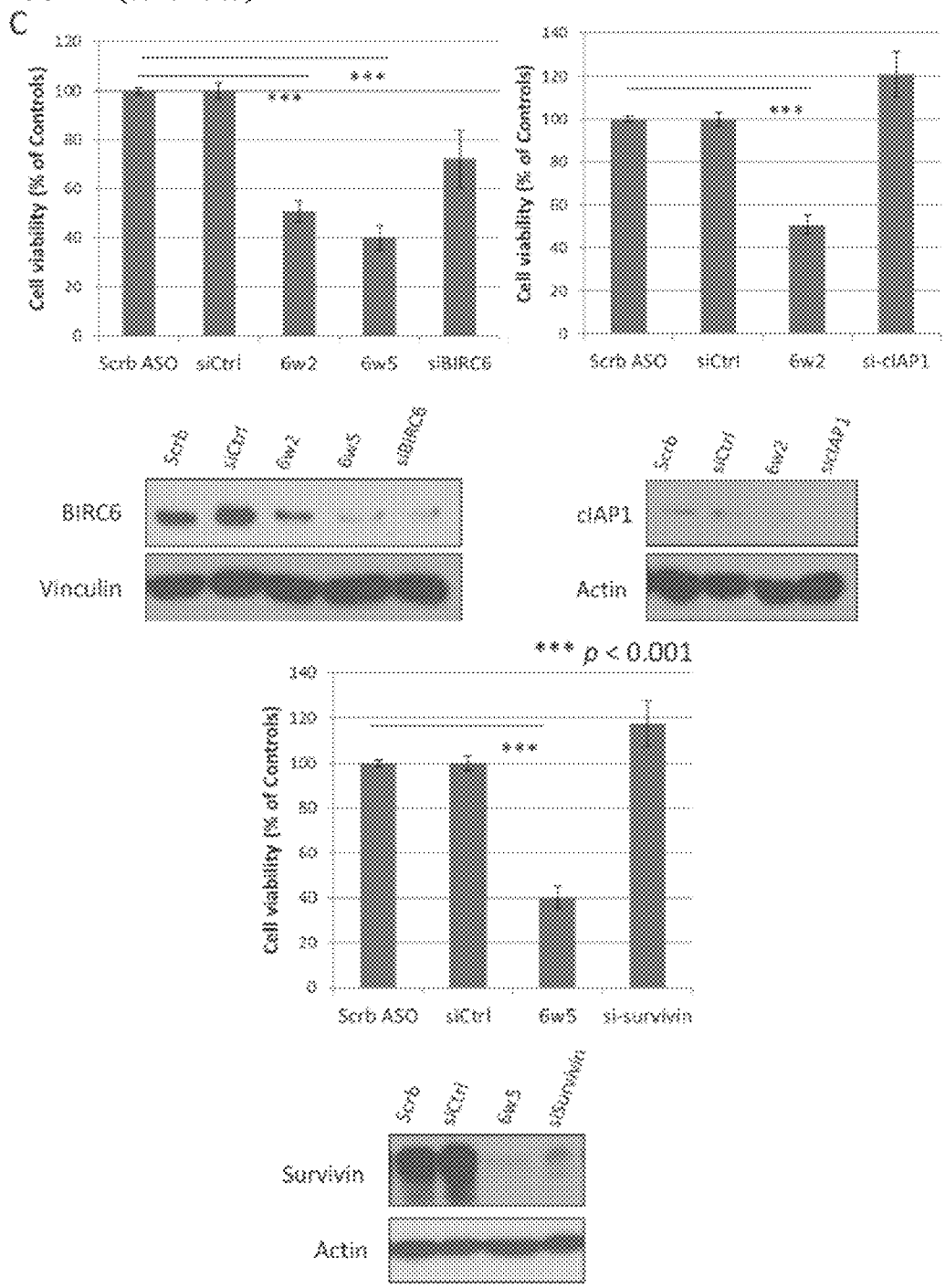

A

B

C

D

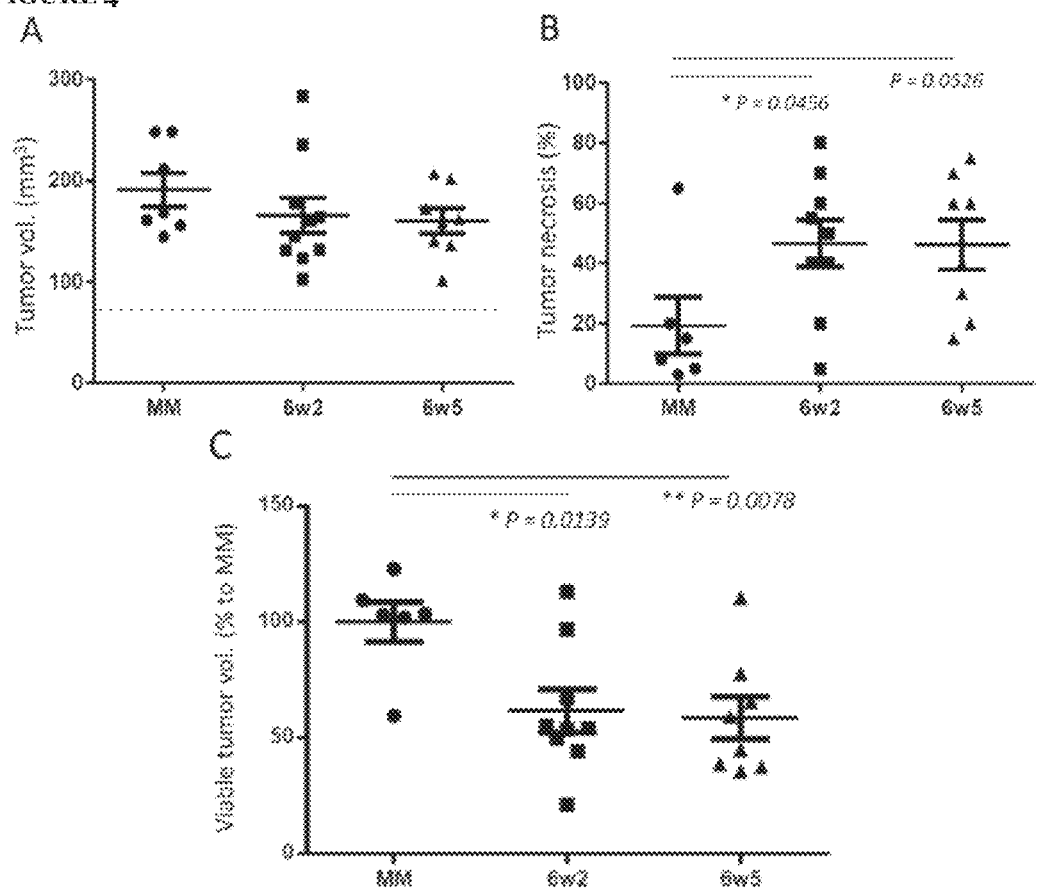

F

A

| Survivin | | | |
|---|---|---|---|
| Clinical stages | Benign | T1-2 | T3-4 |
| Mean staining | 1.63 | 1.86 | 2.12 |
| Std. Error | 0.11 | 0.11 | 0.07 |
| N | 32 | 55 | 91 |

B

| XIAP | | | |
|---|---|---|---|
| Clinical stages | Benign | T1-2 | T3-4 |
| Mean staining | 1.56 | 1.67 | 1.81 |
| Std. Error | 0.16 | 0.12 | 0.07 |
| N | 32 | 55 | 91 |

C

| cIAP1 | | | |
|---|---|---|---|
| Clinical stages | Benign | T1-2 | T3-4 |
| Mean staining | 2.94 | 2.67 | 2.90 |
| Std. Error | 0.04 | 0.05 | 0.03 |
| N | 32 | 55 | 86 |

A

B

A

B

A

B

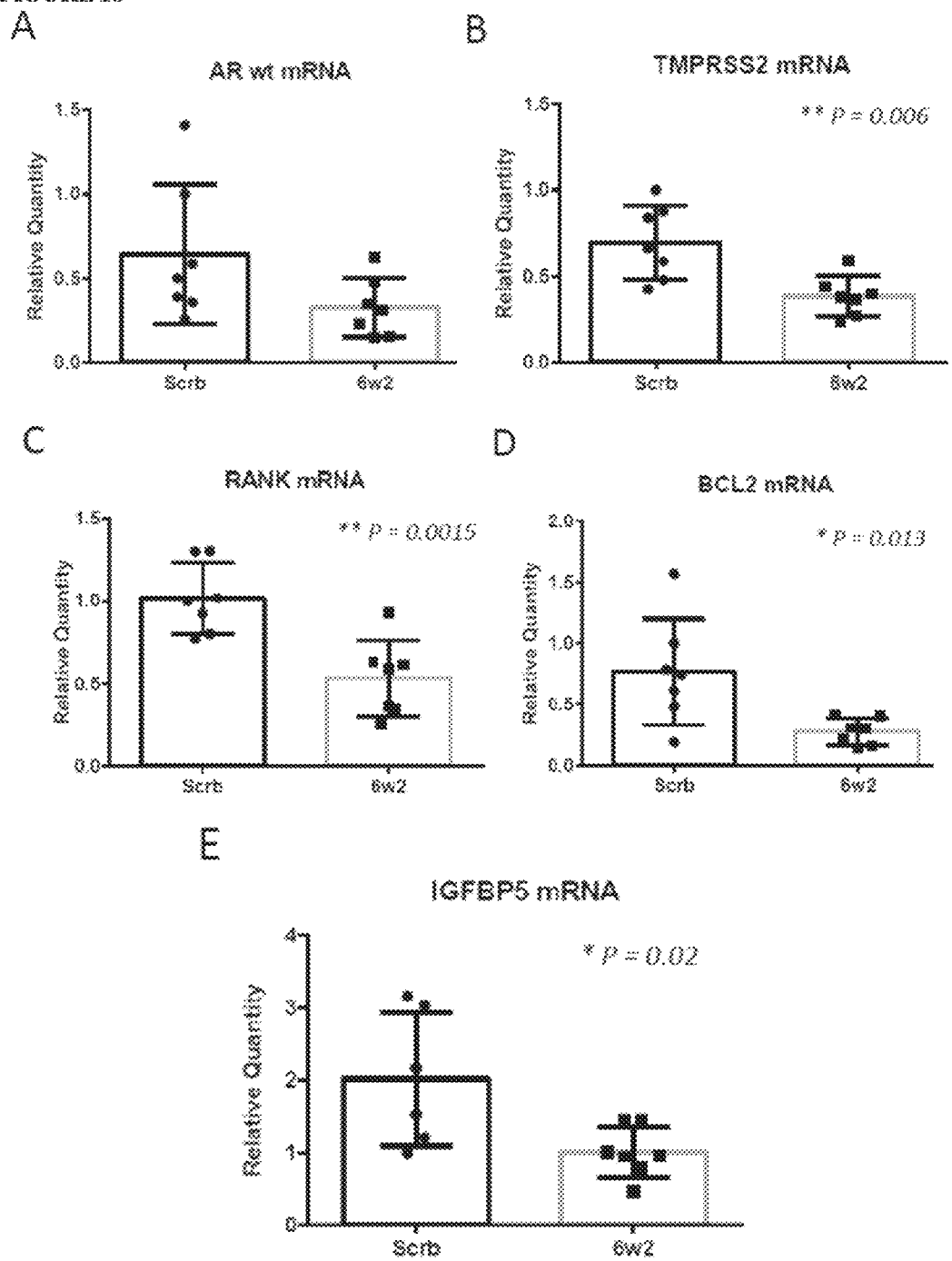

DUAL TARGETING ANTISENSE OLIGONUCLEOTIDES AS APOPTOTIC INHIBTOR THERAPEUTIC COMPOSTIONS AND METHODS FOR THEIR USE IN THE TREATMENT OF CANCER

CROSS REFERENCE TO RELATED APPLICATION

This application claims the benefit of U.S. Provisional Patent Application Ser. No. 62/193,568 filed on 16 Jul. 2015, entitled "DUAL TARGETING ANTISENSE OLIGONUCLEOTIDES AS APOPTOTIC INHIBITOR THERAPEUTIC COMPOSTIONS AND METHODS FOR THEIR USE IN THE TREATMENT OF CANCER", which application is incorporated by reference herein in its entirety.

TECHNICAL FIELD

The present invention provides compounds, compositions and methods for modulating the expression of human Inhibitors of Apoptosis (IAPs). In particular, this invention relates to dual-targeting antisense oligonucleotides (dASOs) capable of modulating human BIRC6 and cIAP1 or survivin mRNA expression, and their uses and methods for the treatment of various indications, including various cancers. In particular the invention relates to therapies and methods of treatment for cancers such as prostate cancer, including castration-resistant prostate cancer (CRPC).

BACKGROUND

Prostate cancer is the most common non-cutaneous cancer and the second leading cause of cancer-related deaths for males in the Western world (Siegel R, et al., 2012, 62(1): 10-29). Prostate cancers are initially androgen-dependent, and while androgen deprivation therapy (ADT) can induce marked tumor regression, resistance to ADT inevitably emerges, leading to castration-resistant prostate cancer (CRPC). The current standard care for treating CRPC is systemic, docetaxel-based chemotherapy, increasing the overall survival of patients by about 2 months compared to mitoxantrone-based therapy (Petrylak D P, et al., N Engl J Med. 2004; 351(15):1513-1520; Tannock I F, et al., N Engl J Med. 2004; 351(15):1502-1512). Recently, sipuleucel-T, cabazitaxel, abiraterone, MDV3100 and Radium-223 have shown more prolonged overall survival benefit and are approved by the FDA for treatment of the disease (Bishr M and Saad F., Nat Rev Urol. 2013; 10(9):522-528). However, none of these drugs are curative; they incrementally improve overall survival. The establishment of more effective therapeutic targets and drugs, specifically those targeting the molecular drivers of metastatic CRPC, is of critical importance for improved disease management and patient survival (Lin D, et al., Curr Opin Urol. 2013; 23(3):214-219).

Apoptosis, a cell death-inducing process important in the regulation of cell numbers in normal tissues, can be triggered by a variety of death signals from both extracellular and intracellular origins, and involves activation of caspases (intracellular cysteine proteases) that mediate the execution of apoptosis (Hensley P, et al., Biol Chem. 2013; 394(7): 831-843). Human cancers are characterized by resistance to apoptosis, intrinsic or acquired, considered to be a key factor underlying resistance to therapeutic intervention, and promising new strategies have been developed based on drug-induced apoptosis (Gleave M, et al., Cancer Chemother Pharmacol. 2005; 56 Suppl 1:47-57). The treatment resistance of CRPC is thought to be based on an increased resistance to apoptosis by the prostate cancer cells and may be addressed by targeting anti-apoptotic genes and their products (Zielinski R R, et al., Cancer J. 2013; 19(1):79-89).

The Inhibitors of Apoptosis (IAP) form a family of functionally and structurally related proteins that have a major role in cell death regulation. They act as endogenous apoptosis inhibitors by binding to caspases, thereby suppressing apoptosis initiation. The human IAP family consists of 8 members that are characterized by the presence of 1 to 3 baculovirus inhibitor of apoptosis repeat (BIR) motifs that are involved in the binding of IAPs to caspases. There is increasing evidence that IAPs also affect other cellular processes, such as ubiquitin-dependent signalling events that activate nuclear factor κB (NFκB) transcription factors, which in turn drive the expression of genes important in cellular processes such as cell survival (Gyrd-Hansen M and Meier P. Nat Rev Cancer. 2010; 10(8):561-574). Due to their ability to control cell death and elevated expression in a variety of cancer cell types, IAP proteins are attractive targets for the development of novel anti-cancer treatments (de Almagro M C and Vucic D. Exp Oncol. 2012; 34(3): 200-211). Four IAP members, i.e. XIAP, survivin, cIAP1 and cIAP2, have been reported to be up-regulated in prostate cancer (Krajewska M, et al., Clin Cancer Res. 2003; 9(13): 4914-4925). Survivin in particular is promising as a potential therapeutic target for the disease (Rodriguez L, et al., Biochem Pharmacol. 2013; 86(11):1541-1554 Carrasco R A, et al., Mol Cancer Ther. 2011; 10(2):221-232).

The BIRC6 gene (BRUCE/APOLLON) encodes a 528 kDa protein in mammals, consisting of a single N-terminal BIR domain and a C-terminal ubiquitin-conjugating (UBC) domain; the latter has chimeric E2/E3 ubiquitin ligase activity as well as anti-apoptotic activity (Bartke T, et al., Mol Cell. 2004; 14(6):801-811). Through its BIR domain, BIRC6 protein can bind to active caspases, including caspases-3, 6, 7 and 9 and such interactions have been shown to underlie its ability to inhibit the caspase cascade and ultimately apoptosis (Bartke T, et al., Mol Cell. 2004; 14(6):801-811). Through its UBC domain, BIRC6 facilitates proteasomal degradation of pro-apoptotic proteins, including caspase-9 (Hao Y, et al., Nat Cell Biol. 2004; 6(9):849-860), SMAC/DIABLO (Hao Y, et al., Nat Cell Biol. 2004; 6(9):849-860; Qiu X B and Goldberg A L. J Biol Chem. 2005; 280(1):174-182), and HTRA2/OMI (Bartke T, et al., Mol Cell. 2004; 14(6):801-811; Sekine K, et al., Biochem Biophys Res Commun. 2005; 330(1):279-285). Elevated expression of BIRC6 has been found in a variety of cancers, i.e. childhood de novo acute myeloid leukemia (Sung K W, et al., Clin Cancer Res. 2007; 13(17):5109-5114), colorectal cancer (Bianchini M, et al., Int J Oncol. 2006; 29(1):83-94), neuroblastoma (Bartke T, et al., Mol Cell. 2004; 14(6):801-811; Lamers F, et al., BMC Cancer. 2012; 12:285), melanoma (Tassi E, et al., Clin Cancer Res. 2012; 18(12):3316-3327) and non-small cell lung cancer (Dong X, et al., J Thorac Oncol. 2013; 8(2):161-170). Furthermore, BIRC6 has been implicated in maintaining resistance against cell death stimuli [Chen Z, et al., Biochem Biophys Res Commun. 1999; 264(3):847-854; Chu L, et al., Gene Ther. 2008; 15(7):484-494). In contrast to other IAPs, BIRC6 has been shown to have a cytoprotective role, essential for survival of mammalian cells (Hao Y, et al., Nat Cell Biol. 2004; 6(9):849-860; Qiu X B, et al., EMBO J. 2004; 23(4):800-810). BIRC6 is also known for its essential role in regulating cytokinesis, a final event of cell division (Pohl C and Jentsch S. Cell. 2008; 132(5):832-845). The dual roles of BIRC6 in cell death and division processes resemble those of survivin, and render it a promising target for therapy of a variety of cancers (Martin S J. Nat Cell Biol. 2004; 6(9):804-806).

Therapeutic options for castration resistant prostate cancer (CRPC) treatment have changed considerably with the recent FDA approvals of newer agents that improve patient survival. In particular, Enzalutamide (ENZ), a second generation androgen receptor antagonist approved for treating metastatic CRPC in post-docetaxel and more recently, pre-docetaxel setting. However, within 2 years of clinical practice, development of ENZ resistance was evident in majority of patients (Claessens et al. 2014) and no known therapies were shown to be effective to ENZ-resistant CRPC to-date. Thus, a novel therapeutic agent that can effectively suppress ENZ-resistant CRPC would be useful.

SUMMARY

The present invention is based in part on the discovery that the inhibition of BIRC6 expression and the inhibition of cIAP1 expression with dual-targeting antisense oligonucleotide (dASO) 6w2 (5'-CTGCAGCATCATGTGGACT-'3-SEQ ID NO:1) may be useful in the treatment of cancer. Similarly, the invention is also based in part of the discovery that the inhibition of BIRC6 expression and the inhibition of suvivin expression with dASO 6w5 (5'-CAGGT-GAAACACTGGGACA-'3-SEQ ID NO:2) may be useful in the treatment of cancer. The combined inhibition of BIRC6 expression with the inhibition of cIAP1 expression or combined inhibition of BIRC6 expression with the inhibition of survivin expression leads to reduced proliferation of cancer cells. Furthermore, that reduction in proliferation extends to castration-resistant prostate cancer (CRPC).

In a first aspect, a composition is provided a method for the treatment of a cancer cell, the method including administering an oligonucleotide of SEQ ID NO:1 or SEQ ID NO:2 to the cell.

In a further aspect, there is provided a method including administering a dual-targeting antisense oligonucleotides (dASO) of SEQ ID NO:1 or SEQ ID NO:2.

In a further aspect, there is provided a dual-targeting antisense oligonucleotide (dASO), wherein the oligonucleotide has a sequence selected from the following: (a) CTGCAGCATC ATGTGGACT (SEQ ID NO: 1); and (b) CAGGTGAAAC ACTGGGACA (SEQ ID NO: 2).

In a further aspect, there is provided a dual-targeting antisense oligonucleotide (dASO) of SEQ ID NO:1 or SEQ ID NO:2 for use in the treatment of cancer.

In a further aspect, there is provided a dual-targeting antisense oligonucleotide (dASO) of SEQ ID NO:1 or SEQ ID NO:2 for inhibiting expression of one of more of BIRC6 and cIAP1 or survivin.

In a further aspect, there is provided a pharmaceutical composition, the composition including (a) dual-targeting antisense oligonucleotide (dASO) of SEQ ID NO:1 or SEQ ID NO:2; and (b) a pharmaceutically acceptable carrier.

In a further aspect, there is provided a use of a dASO of SEQ ID NO:1 or SEQ ID NO:2 in the preparation of a medicament for the treatment of cancer.

In a further aspect, there is provided a use of a dASO of SEQ ID NO:1 or SEQ ID NO:2 in the preparation of a medicament for inhibiting expression of one of more of BIRC6 and cIAP1 or survivin.

In a further aspect, there is provided a use of a dASO) of SEQ ID NO:1 or SEQ ID NO:2 for the treatment of cancer.

In a further aspect, there is provided a use of a dASO of SEQ ID NO:1 or SEQ ID NO:2 for inhibiting expression of one of more of BIRC6 and cIAP1 or survivin.

In accordance with a further aspect, there is provided a commercial package including (a) an antisense oligonucleotide sequence described herein and a pharmaceutically acceptable carrier; and (b) instructions for the use thereof for modulating IAP activity.

In a further aspect, there is provided a commercial package, including: (a) dASO of SEQ ID NO:1 or SEQ ID NO:2; and (b) instructions for the treatment of cancer.

In accordance with a further aspect, there is provided a method for modulating IAP activity, the method comprising administering a dual-targeting antisense oligonucleotides (dASO) of SEQ ID NO:1 or SEQ ID NO:2 and a pharmaceutically acceptable carrier; and (b) instructions for the use thereof.

In accordance with a further aspect, there is provided a method for modulating IAP activity in a cell, the method comprising administering a dual-targeting antisense oligonucleotides (dASO) of SEQ ID NO:1 or SEQ ID NO:2 to the cell.

In accordance with a further aspect, there is provided a use of a dual-targeting antisense oligonucleotides (dASO) of SEQ ID NO:1 or SEQ ID NO:2 for modulating IAP activity.

In accordance with a further aspect, there is provided a use of a dual-targeting antisense oligonucleotides (dASO) of SEQ ID NO:1 or SEQ ID NO:2 in the manufacture of a medicament for modulating IAP activity.

The dASO may further include a modified internucleoside linkage. The modified internucleoside linkage may be a peptide-nucleic acid linkage, a morpholino linkage, a N3' to P5' phosphoramidate linkage, a methylphosphonate linkage or a phosphorothioate linkage. The dASO may further include a modified sugar moiety. The modified sugar moiety may be a 2'-O-alkyl oligoribonucleotide. The dASO may further have a 2'MOE gapmer modification. The dASO may further include a modified nucleobase. The modified nucleobase may be a 5-methyl pyrimidine or a 5-propynyl pyrimidine.

The cell may be a human cell. The the cancer may be characterized by elevated expression of one of more of BIRC6 and cIAP1 or survivin. The cancer may be selected from one or more of the following: prostate cancer; childhood de novo acute myeloid leukemia; colorectal cancer; neuroblastoma; melanoma; and non-small cell lung cancer. The prostate cancer may be castration-resistant prostate cancer (CRPC). The prostate cancer may be enzalutamide (ENZ) resistant CRPC.

The dASO may be substantially complementary to the mRNA of BIRC6 and cIAP1. The dASO may be administered intravenously. The dASO may be topically administered to a tissue. The dASO may be mixed with lipid particles prior to administration. The dASO may be encapsulated in liposomes prior to administration.

BRIEF DESCRIPTION OF THE DRAWINGS

FIG. 16 shows dASO 6w2 treatment was associated with reduced mRNA expressions of pro-survival pathways in tumors. Implicated survival pathways include androgen receptor (A) and TMPRSS2 (B) in androgen receptor signaling, RANK (C) and BCL2 (D) in NFkB signaling, and IGFBP5 (E) in IGFR signaling. Relative mRNA expressions were determined by QPCR. n=7 per group. Error bars=mean±SD.

DETAILED DESCRIPTION

Figure 1:
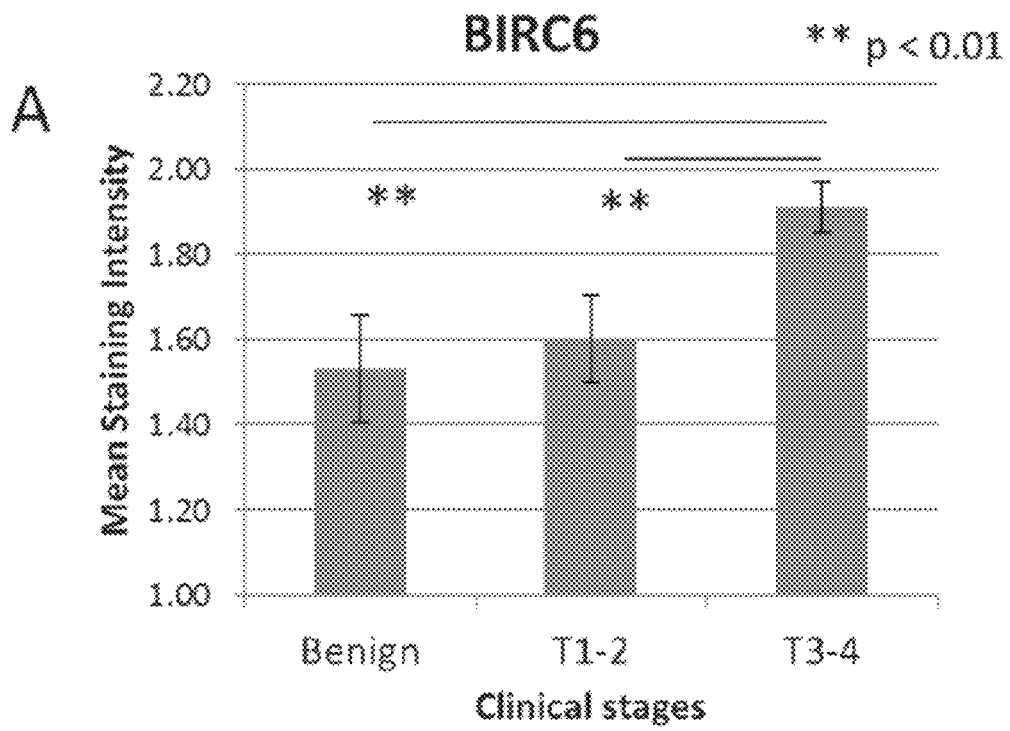
FIG. 1 shows elevated BIRC6 expression is associated with advanced stages of prostate cancer: co-upregulation of other IAP members, wherein (A) shows a correlation of immunohistochemical staining intensity of BIRC6 and clinical (T) stages of prostate cancer (mean staining intensity±S.E.M.) and (B-D) show correlations of BIRC6 immunohistochemical staining intensity with the absence and presence of poor prognostic factors, such as recurrence of PSA, lymph node metastasis and prostatic capsule invasion. The statistical significance of positive trends was determined by the Chi square test for trend. (E) Representative images of correlated expressions between BIRC6 and survivin, XIAP and cIAP1. 20× magnification, scale bar, 100 μm.
Figure 1:
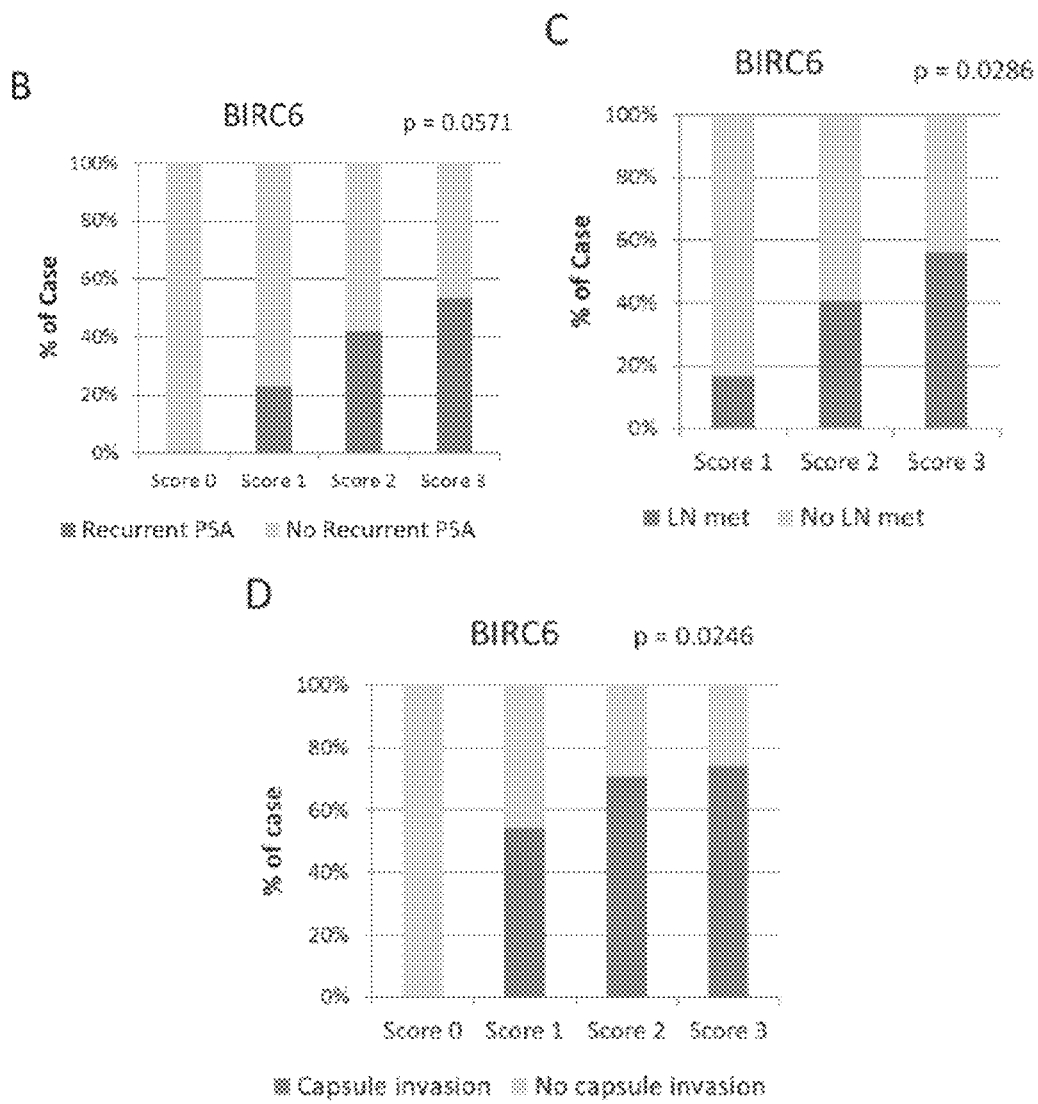
Figure 1:
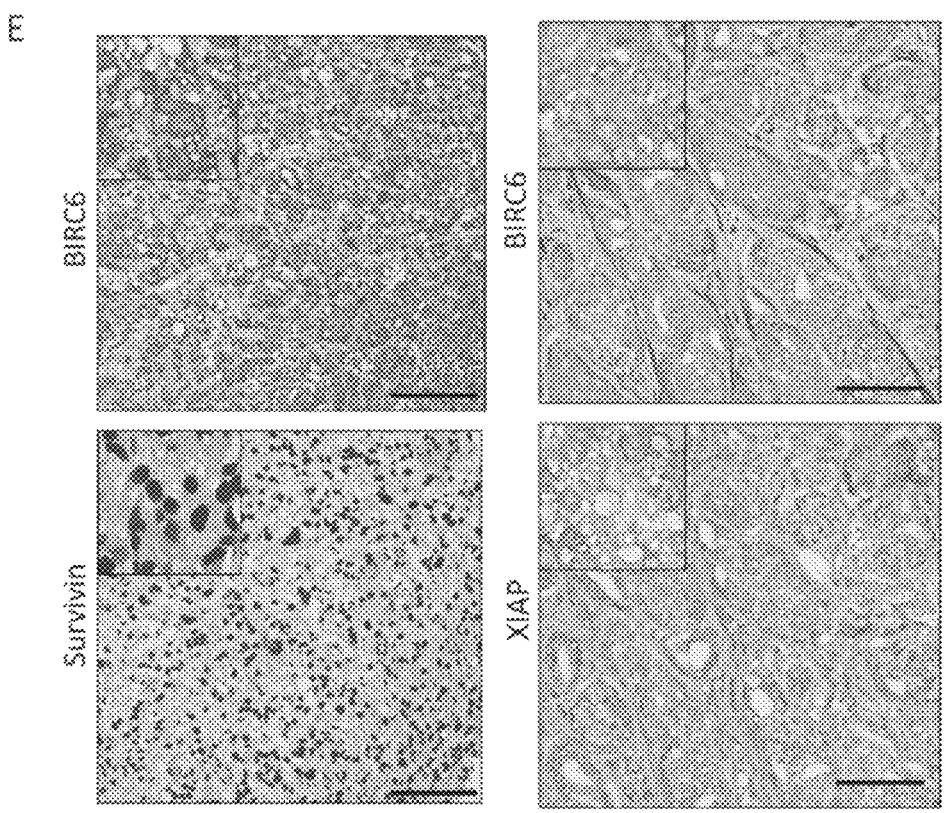
Figure 1E:
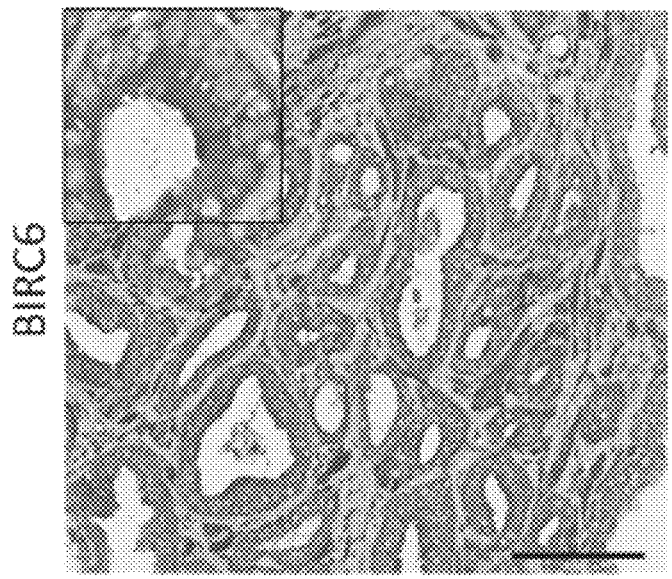
Figure 1E:
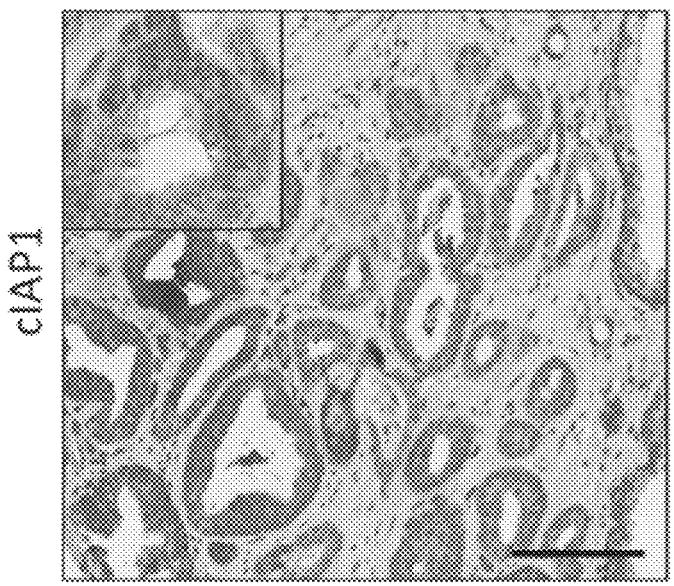

Any terms not directly defined herein shall be understood to have the meanings commonly associated with them as understood within the present field of art. Certain terms are discussed below, or elsewhere in the specification, to provide additional guidance to the practitioner in describing the compositions, devices, methods and the like of embodiments, and how to make or use them. It will be appreciated that the same thing may be said in more than one way. Consequently, alternative language and synonyms may be used for any one or more of the terms discussed herein. No significance is to be placed upon whether or not a term is elaborated or discussed herein. Some synonyms or substitutable methods, materials and the like are provided. Recital of one or a few synonyms or equivalents does not exclude use of other synonyms or equivalents, unless it is explicitly stated. Use of examples in the specification, including examples of terms, is for illustrative purposes only and does not limit the scope and meaning of the embodiments described herein.

A method is provided for "treating" a cancer cell, wherein treating is meant to encompass preventing proliferation of the cell, ameliorating symptoms associated with the cancer, and eradicating the cancer cell. The term "treating" as used herein is also meant to include the administration at any stage of the cancer, including early administration of a compound or late administration. A person of skill in the art would appreciate that the term "ameliorating" is meant to include the prospect of making a cancer more tolerable for a subject afflicted therewith (for example, by reducing tumour load). A person of skill in the art would also appreciate that the term "eradication" with regards to cancer would include elimination of the cancer cells in whole or in part from a subject. Accordingly, as used herein "treatment" may refer to the prevention of cancer cell proliferation in a subject, the amelioration of symptoms associated with the cancer, the eradication of the cancer from a subject, or combinations thereof.

Antisense oligonucleotide compounds are typically single stranded RNA compounds which bind to complementary RNA compounds, such as target mRNA molecules, and block translation from the complementary RNA compounds by sterically interfering with the normal translational machinery. This process is usually passive, in that it does not require or involve additional enzymes to mediate the RNA interference process. Specific targeting of antisense RNA compounds to inhibit the expression of a desired gene may generally involve designing the antisense RNA compound to have a homologous, complementary sequence to the desired gene. Perfect homology is not necessary for the RNA interference effect. In one embodiment of the invention, the antisense RNA compounds include any RNA compound with sufficient complementary homology to bind to the BIRC6 mRNA transcript and the cIAP1 transcript causing a reduction in translation of the BIRC6 and cIAP1 proteins. In another embodiment of the invention, the antisense RNA compounds include any RNA compound with sufficient complementary homology to bind to the BIRC6 mRNA transcript and the survivin transcript causing a reduction in translation of the BIRC6 and survivin proteins. The antisense compounds be modified to enhance the stability of the oligonucleotides, particularly for in vivo use. Numerous examples of methods for designing and optimizing antisense RNA compounds are found in the journal literature—i.e. (Pan and Clawson 2006; Patzel 2007; Peek and Behlke 2007). Perfect sequence complementarity is not necessary for the antisense compound to modulate expression of the target gene. The present inventors provide non-limiting examples of antisense compounds which modulate the expression of BIRC6, cIAP1 and survivin.

Antisense oligonucleotide sequences as described herein or for use as described herein may be administered by means of a medical device or appliance such as an implant, graft, prosthesis, stent, etc. Also, implants may be devised which are intended to contain and release such compounds or compositions. An example would be an implant made of a polymeric material adapted to release the compound over a period of time.

Dual-targeting antisense oligonucleotides (dASOs) that simultaneously target BIRC6 and another co-upregulated IAP member are provided herein. Encompassed herein, is the use of dASOs 6w2 and 6w5 for administration to a cell. The 6w2 and 6w5 dASOs as used in the examples had a modified internucleoside linkages. In particular, the dASOs had phosphorothioate linkages between all nucleosides. 6w2 may have combined inhibition of BIRC6 expression and cIAP1 expression. 6w2 and 6w5 are both 19-mer oligonucleotides with modified phosphorothioate linkages. However, variations of 6w2 and 6w5 may also have unmodified phosphodiester linkages or partially modified linkages (i.e. any integer between 1 and 18 phosphorothioate linkage(s) or other modified linkages). Alternative modifications are also known in the art.

A phosphorothioate oligonucleotide bond modification alters the phosphate linkage by replacing one of the non-bridging oxygens with sulfur. The introduction of phosphorothioate linkages alters the chemical properties of the oligonucleotide. In particular, the addition of phosphorothioate linkages reduces nuclease degradation of the oligonucleotide and thereby increasing the half-life in situ. Accordingly, this modification is particularly useful for antisense oligonucleotides, which when introduced into cells or biological matrices can interact with target nucleic acids to silence the expression of a particular transcript. Oligonucleotides containing phosphorothioate linkages accomplish this feat either through direct blockage of translation or enable enzymatic degradation of the target transcript (for example, via RNase H).

Although phosphorothioate linkages provide improved half-life, the introduction of these linkages into an oligonucleotide may also introduce limitations to their function as antisense oligonucleotides. Each phosphorothioate linkage creates a chiral center at each bond, which may result in multiple isomers of the oligonucleotide generated during synthesis and the isomers may have differential characteristics and functional properties. However much of the isomer effects may be mitigated through careful positioning of the modifications or by using additional modifications in conjunction with the phosphorothioate bonds.

One or more of the phosphorothiodiester linkages of the oligonucleotide moiety may be modified by replacing one or both of the two bridging oxygen atoms of the linkage with analogues such as —NH, —CH2, or —S. Other oxygen analogues known in the art may also be used.

A "modified oligonucleotide" as used herein is meant to include oligonucleotides that are substituted or modified. In addition to the naturally occurring primary bases adenine, guanine, cytosine, and thymine, or other natural bases such as inosine, deoxyinosine, and hypoxanthine, there are numerous other modifications. For example, isosteric purine 2'deoxy-furanoside analogues, 2'-deoxynebularine or 2'deoxyxanthosine, or other purine and pyrimidine analogues such as 5-methyl pyrimidine or a 5-propynyl pyrimidine may also be utilized to improve stability and target hybridization.

A "modified sugar" as used herein when discussing an oligonucleotide moiety, a sugar modified or replaced so as to be ribose, glucose, sucrose, or galactose, or any other sugar. Alternatively, the oligonucleotide may have one or more of its sugars substituted or modified in its 2' position, i.e. 2'alkyl or 2'-o-alkyl. An example of a 2'-O-allyl sugar is a 2'-O-methylribonucleotide. Furthermore, the oligonucleotide may have one or more of its sugars substituted or modified to form an α-anomeric sugar.

"Second-generation" oligonucleotides as used herein mat be defined as oligonucleotides that are resistant to degradation by cellular nucleases and capable of hybridizing specifically to their target mRNA with equal or higher affinity than first generation ASOs. An example of a $2^{nd}$ generation ASO is a 2'-O-(2-Methoxyethyl)-RNA (2'MOE gapmer modification). With a 2'-MOE gapmer the 5' and 3' ends may have 2'-MOE modified nucleotides to protect against degradation, but the gap between the 5' and 3' ends may be unmodified phosphodiester linkages. Numerous other chemical modifications have been developed to improve ASOs. For example, morpholino, N3' to P5' phosphoramidate, and methylphosphonate chemical modifications are known in the art (N. Dias, and C. A. Stein 2002). Furthermore, peptide nucleic acids (PNAs) may also be used.

The percent matching to primary and secondary targets are shown below in TABLE A.

TABLE A

Primary and secondary targeted regions and percentage of matching nucleotide sequences for the two dASOs.

| dASO | Primary Target | % match | Secondary target | % match |
|---|---|---|---|---|
| 6w2 | BIRC6 mRNA, nt 9299-9281 | 19/19 (100%), | BIRC2 transcript variant 2 mRNA, nt 955-937 | 18/19 (95%) |
| | | | BIRC2 transcript variant 1 mRNA., nt 678-660 | 18/19 (95%) |
| 6w5 | BIRC6 mRNA nt 12035-12017 | 19/19 (100%), | BIRC5 transcript variant 1-3 mRNA, Nt 282-300 | 16/19 (84%) |

The compounds, as described herein, may be in isolation, or may be linked to or in combination with tracer compounds, liposomes, carbohydrate carriers, polymeric carriers or other agents or excipients as will be apparent to one of skill in the art. In alternate embodiments, such compounds may further comprise an additional medicament, wherein such compounds may be present in a pharmacologically effective amount.

The term "medicament" as used herein refers to a composition that may be administered to a patient or test subject and is capable of producing an effect in the patient or test subject. The effect may be chemical, biological or physical, and the patient or test subject may be human, or a non-human animal, such as a rodent (for example, a transgenic mouse, a mouse or a rat), dog, cat, cow, sheep, horse, hamster, guinea pig, rabbit or pig. The medicament may be comprised of the effective chemical entity alone or in combination with a pharmaceutically acceptable excipient.

The term "pharmaceutically acceptable excipient" may include any and all solvents, dispersion media, coatings, antibacterial, antimicrobial or antifungal agents, isotonic and absorption delaying agents, and the like that are physiologically compatible. An excipient may be suitable for intravenous, intraperitoneal, intramuscular, subcutaneous, intrathecal, topical or oral administration. An excipient may include sterile aqueous solutions or dispersions for extemporaneous preparation of sterile injectable solutions or dispersion. Use of such media for preparation of medicaments is known in the art.

Compositions or compounds according to some embodiments described herein may be administered in any of a variety of known routes. Examples of methods that may be suitable for the administration of a compound include orally, intravenously, inhalation, intramuscular, subcutaneous, topical, intraperitoneal, intra-rectal or intra-vaginal suppository, sublingual, and the like. The compounds described herein may be administered as a sterile aqueous solution, or may be administered in a fat-soluble excipient, or in another solution, suspension, patch, tablet or paste format as is appropriate. A composition comprising the compounds described herein may be formulated for administration by inhalation. For instance, a compound may be combined with an excipient to allow dispersion in an aerosol. Examples of inhalation formulations will be known to those skilled in the art. Other agents may be included in combination with the compounds described herein to aid uptake or metabolism, or delay dispersion within the host, such as in a controlled-release formulation. Examples of controlled release formulations will be known to those of skill in the art, and may include microencapsulation, embolism within a carbohydrate or polymer matrix, and the like. Other methods known in the art for making formulations are found in, for example, "Remington's Pharmaceutical Sciences", (19th edition), ed. A. Gennaro, 1995, Mack Publishing Company, Easton, Pa.

The dosage of the compositions or compounds of some embodiments described herein may vary depending on the route of administration (oral, intravenous, inhalation, or the like) and the form in which the composition or compound is administered (solution, controlled release or the like). Determination of appropriate dosages is within the ability of one of skill in the art. As used herein, an "effective amount", a "therapeutically effective amount", or a "pharmacologically effective amount" of a compound refers to an amount of the dASO 6w2 present in such a concentration to result in a therapeutic level of the compound delivered over the term that the compound is used. This may be dependent on the mode of delivery, time period of the dosage, age, weight, general health, sex and diet of the subject receiving the compound. Methods of determining effective amounts are known in the art. It is understood that it could be potentially beneficial to restrict delivery of the compounds described herein to the target tissue or cell in which inhibition of BIRC6 expression and/or the inhibition of cIAP1 expression is desired. It is also understood that it may be desirable to target the compounds described herein to a desired tissue or cell type. The compounds described herein may thus be coupled to a targeting moiety. The compounds may be coupled to a cell uptake moiety. The targeting moiety may also function as the cell uptake moiety.

In general, antisense oligonucleotides as described herein may be used without causing substantial toxicity. Toxicity of the compounds as described herein can be determined using standard techniques, for example, by testing in cell cultures or experimental animals and determining the therapeutic index, i.e., the ratio between the LD50 (the dose lethal to 50% of the population) and the LD100 (the dose lethal to 100% of the population). In some circumstances however, such as in severe disease conditions, it may be appropriate to administer substantial excesses of the compositions. Some antisense oligonucleotides as described herein may be toxic at some concentrations. Titration studies may be used to determine toxic and non toxic concentrations. Toxicity may be evaluated by examining a particular antisense oligonucleotide's specificity across cell lines. Animal studies may be used to provide an indication if the compound has any effects on other tissues.

In some embodiments, antisense oligonucleotides as described herein may be used, for example, and without limitation, in combination with other treatment methods for at least one indication selected from malignancies in which elevated expression of BIRC6, cIAP1 or survivin is observed. These include, but are not limited to, prostate cancer, childhood de novo acute myeloid leukemia, colorectal cancer, neuroblastoma, melanoma, and non-small cell lung cancer in mammals, including humans. For example, antisense oligonucleotides and may be used as neoadjuvant (prior), adjunctive (during), and/or adjuvant (after) therapy with surgery, radiation (brachytherapy or external beam), or other therapies (eg. HIFU).

Methods and Materials

The following methods and materials were employed with respect to the EXAMPLES described herein.

Cell Lines

PC-3 human prostate cancer cell lines were obtained from the American Type Culture Collection (1991, ATCC). C4-2 cells were kindly provided by Dr. L. W. K. Chung (1992, MD Anderson Cancer Center, Houston, Tx). They were maintained as monolayer cultures in RPMI-1640 (Gibco BRL™, Gaithersburg, Md.) supplemented with 10% fetal bovine serum (FBS). Prior to usage, cells were determined to be *mycoplasma* free (*Mycoplasma* Detection Kit™, Invitrogen™ #rep-pt2) and were not authenticated.

Tissue Microarray (TMA) Construction and Immunohistochemistry (IHC)

Prostate specimens (60 benign prostate samples, 137 primary tumors with no lymph node metastasis, 30 primary tumors with lymph node metastasis, 65 neo-adjuvant treated primary tumors, 67 CRPCs) were obtained from the Vancouver Prostate Centre Tissue Bank following written informed patients' consent and institutional study approval. All samples had been obtained through radical prostatectomy except the CRPC samples that were obtained through transurethral resection of prostate (TURP). TMAs were constructed as previously described (Thomas C, et al., Molecular cancer therapeutics. 2011; 10(2):347-359). Immunohistochemical staining using rabbit polyclonal antibody against BIRC6, rabbit monoclonal antibody against Survivin, monoclonal antibody against cIAP1 and rabbit polyclonal antibody against XIAP was conducted using a Ventana autostainer (model Discover XT™; Ventana Medical Systems™, Tucson, Ariz.) with an enzyme-labelled biotin-streptavidin system and a solvent-resistant DAB Map kit (Ventana™). Descriptively, 0 represents no staining by any tumor cells, 1 represents a faint or focal, questionably present stain, 2 represents a stain of convincing intensity in a minority of cells and 3 a stain of convincing intensity in a majority of cells.

Dual IAP-targeting ASO Design and Validation

Dual IAP-targeting ASOs (dASOs) were designed as 20-mers with perfect complementary matches to BIRC6 mRNA sections and containing no more than 3 base mismatches to the second target mRNA (i.e. cIAP1 or survivin). Sequence alignment to each pair of targeted genes was performed using Clustalw (http://www.genome.jp/tools/clustalw/) and BLAST 2 Sequence in NCBI (http://www.ncbi.nlm.nih.gov/blast/bl2seq/wblast2.cgi) to identify sequences with highest complementarities. ASOs with full phosphorothioate-modified backbone were designed. The dASO knock-down efficacy of six designed dASOs was tested by determining target protein expression 48 hours after transfection using Western blot analysis. Two dASO candidates (6w2 and 6w5) were selected for further studies: dASO 6w2 (SEQ ID NO:1 5'CTGCAGCATCATGTG-GACT) and dASO 6w5 (SEQ ID NO:2 5'CAGGT-GAAACACTGGGACA). Non-targeting control ASOs: Scramble (Scrb) B control (SEQ ID NO:3 5'CCTTCCCT-GAAGGTTCCTCC), and mismatched (MM) control (SEQ ID NO:4 5'CAGCAGCAGAGTATTTATCAT). Further information on dASO targeting regions and presence of mismatches to target mRNA are shown in TABLE A.

A person of skill in the art based on the general knowledge in the art and the information provided herein would be able to synthesize the dual-targeting ASOs described herein or modify the dASOs described herein.

siRNA and ASO Transfections

Small interfering RNAs (siRNAs) targeting cIAP1 (si-cIAP1, siGENOME SMARTpool™ human BIRC2), survivin (si-Surv, siGENOME SMARTpool™ human BIRC5), BIRC6 [si-BIRC6, 5'-GUU-UCA-AAG-CAG-GAU-GAU-G-dTdT-3'] (Ren J, et al., Proc Natl Acad Sci USA. 2005; 102(3):565-570) and negative control (siCtrl) siRNAs were purchased from Dharmacon™ (Cat #M-004390-02-0005, M-003459-03-0005 and D001810-10-05, Chicago, Ill.). Cells were transfected with siRNA (2 nM for si-survivin and si-cIAP1, 10 nM for si-BIRC6) or ASO (100-200 nM) for 72 hours using oligofectamin reagent (Invitrogen™) following the manufacturer's instructions.

Western Blotting

Cell lysates were prepared using cell lysis buffer (1% NP-40, 0.5% sodium deoxycholic acid) supplemented with a protease inhibitor cocktail (Roche™, Nutley, N.J.). For detection of BIRC6 (528 kDa), 10 µg whole cell lysate was resolved in 5% SDS-polyacrylamide gel and electrotransferred to a PVDF membrane in tris (25 mM), glycine (191.5 mM), methanol (10%), SDS (0.05%) buffer at 40V overnight at 4° C. Membranes were probed with anti-BIRC6 antibody at room temperature for 2.5 hours. For detection of cIAP1 and survivin, lysate was resolved in 10% and 15% SDS-polyacrylamide gel, respectively, and electro-transferred to a PVDF membrane in tris (25 mM), glycine (191.5 mM), methanol (10%) buffer at 100V for 1 hour. Membranes were probed with anti-cIAP1 and anti-survivin antibodies at room temperature for 2.5 hours. Actin or vinculin were used as loading controls and detected on membranes using rabbit anti-actin polyclonal antibody or mouse anti-vinculin antibody.

Annexin V Assay

Apoptosis was detected by fluorescence-activated cell sorter (FACS) analysis with annexin-V conjugated with fluorescein isothiocyanate (Annexin-V-FITC) (Invitrogen™) and propidium iodide (PI) staining following the manufacturer's protocol as previously described (Low C G et al., PLoS One. 2013; 8(2):e55837). Early apoptotic cells were identified as Annexin-V positive, PI negative. Data are presented as means±SD of triplicate experiments.

MTS Cell Viability Assay

C4-2 cells ($1\times10^5$) or PC-3 cells ($2.5\times10^4$) were seeded onto 12-well or 24-well culture plates and transfected the next day. MTS (Promega™, Madison, Mich.) was added to wells at 0, 48, 72 and 96 hours after transfection and incubated for 2 hours at 37° C. Aliquots (100 µl) of the culture medium were transferred to a 96-well plate for measuring absorbance at OD490. Triplicate wells were tested per assay and each experiment was repeated twice.

Cell Proliferation Assay

PC-3 cells ($5\times10^4$) were seeded onto 12-well plates and transfected with ASOs the next day. Cell numbers were counted at 0, 48, 72, 96 hours after transfection using a TC10™ Automated Cell Counter (Bio-rad Laboratories™, Inc, Berkeley, Calif.). Triplicate wells were tested per assay and the experiment was repeated twice. Results are presented as percentage of untreated control values, mean±S.D.

Cell Cycle Analysis

Cell cycle distribution was determined by flow cytometry of PI-stained cells as previously described (Low C G et al., PLoS One. 2013; 8(2):e55837). Cells were fixed at 72 hours after transfection. The proportion of cells in G1, S, and G2-M phases of the cell cycle was determined using a FlowJo Program™ (TreeStar Inc™, Ashland, Oreg.).

4,6-Diamidino-2-phenylindole (DAPI) Staining

PC-3 cells were seeded on cover slips in 12 well-plates and transfected with ASO the next day. After 72 hours of transfection, cells were washed twice with PBS and slides were mounted using VECTASHIELD™ Mounting Medium with DAPI™ (Vector Laboratories™, CA). Cell morphology was examined under a fluorescent microscope (Carl Zeiss™, Germany). Cells exhibiting fragmented nuclear bodies were considered to be undergoing apoptosis. A total of 500 cells were counted in five randomly selected fields per sample using a magnification of 400×.

Dual Luciferase Reporter Assay

PC-3 cells ($7\times10^3$) were seeded onto 96-well plates and co-transfected the next day with 0.05 µg pGL4.32 [luc2P/NF-kB-RE/Hygro] (#E849A, Promega Corp.™, Madison, Wis.), 1 ng pRL-CMV (*Renilla*™) and 100 nM dASOs or 10 nM si-BIRC6 or 2 nM si-cIAP1 using lipofectamine 2000, following the manufacturer's instructions. Cells were incubated with 20 ng/ml TNFα for 5 hours at 37° C. for induction of NFκB signalling. Luciferase activity was assessed with a Dual-luciferase reporter assay system (#E1910, Promega™) at 48 hours after transfection and measured using a Tecan™, Infinite 200Pro™ microplate reader (Tecan™, Männedorf, Switzerland) following the manufacturer's instructions. Transfection efficiency was normalized to *Renilla* luciferase activity. Fold induction of NFκB signaling was calculated as average normalized relative light units of induced cells/average normalized relative light units of non-induced cells. Triplicate wells were tested per assay and the experiment was done in duplicate.

Animal Studies

PC-3 cells ($1\times10^6$) were mixed with matrigel and inoculated subcutaneously in both flanks of 6- to 8-weeks-old NOD-SCID mice under isoflurane anesthesia. When tumors reached a volume of 50-70 mm3, mice were randomized into 3 groups (n=12 tumors per group), control ASO, dASO 6w2 and dASO 6w5. The ASOs were administrated to the mice by intraperitoneal injection once daily for 15 consecutive days at a dose of 10 mg/kg. Tumor volume was measured on day 0 and on day 15, the last day of treatment, using the formula: volume=(width)2×length/2. Mice were euthanized on day 15 and tumors fixed for immunohistochemical staining. Percentage of tumor growth represents the change in tumor volume measured on days 1 and 15. Viable tumor volume refers to total tumor volume×(100%−% of necrotic area), where % of necrotic area was determined by microscopic examination of H&E stained sections. Scoring of BIRC6 was determined on a four-point scale as mentioned above. Ki-67 positive cells were counted in 6-8 randomly selected fields (40× magnification) and results are presented as percentage of cells with Ki-67 positive nuclei compared to the total number of cells. Statistical analyses Comparisons of two groups were made using the Student t test. Analyses of correlation between IAP members were performed using a Spearman non-parametric test. Analyses of correlation between BIRC6 expression trend and various prognostic factors were carried out using the Chi square test for trend. Statistical analyses were performed using GraphPad Prism™ 4.0 (GraphPad™). Results with a p<0.05 were considered significant.

Patient Derived Xenograft (PDX) Studies

The responses of a panel of 8 PDX models to ENZ were examined. One of the models, LTL313BR, was a castration relapsed subline of patient derived prostate cancer cells which was found to be highly resistant to ENZ. Development of PDX LTL313B and LTL313BR tumor lines. LTL313BR was accomplished using castration relapse (3-4 months post castration) of parental LTL313B (www.livingtumorlab.com).

Its parental hormone naïve tumor line LTL313B was sensitive to ENZ. The dASO 6w2 was tested for its ability to impede ENZ-resistant CRPC growth. The expression of BIRC6 in relation to ENZ resistance (LTL313B vs LTL313BR) was examined, followed by efficacy study using a larger cohort (N=30) of ENZ-resistant LTL313BR. Finally, the effect of dASO treatment on LTL313BR apoptosis and survival signaling were also investigated.

EXAMPLES

Example 1

Figure 5:
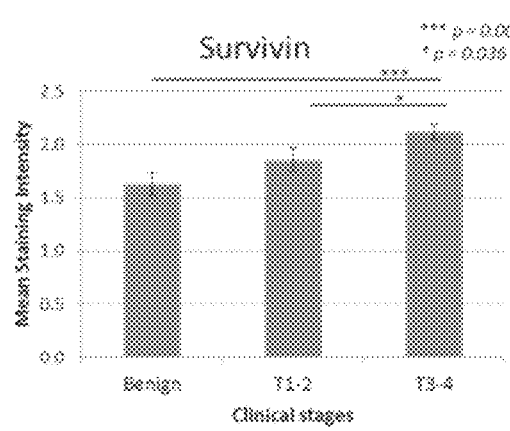
FIG. 5 shows the association of survivin, XIAP and cIAP1 expressions with clinical status and prognostic features of prostate cancer. Analyses of correlation between BIRC6 expression trend and various prognostic factors were carried out using the Chi square test for trend (ns, statistically not significant).
Figure 5:
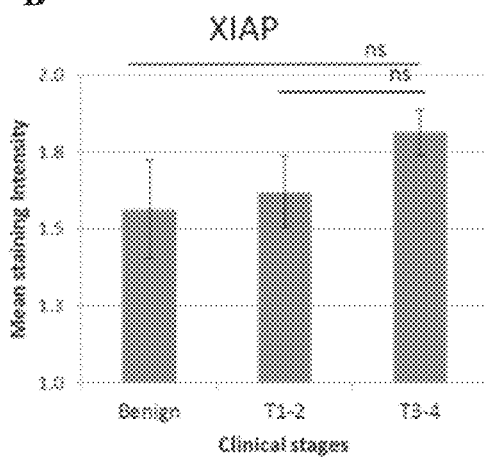
Figure 5:
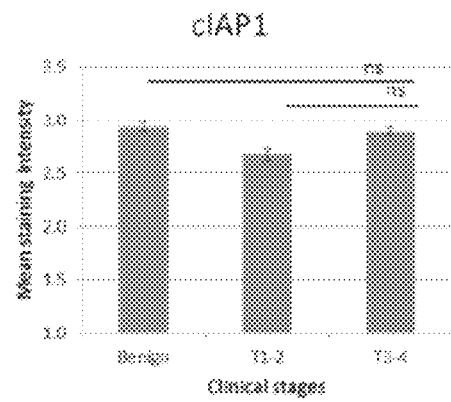
Figure 5:
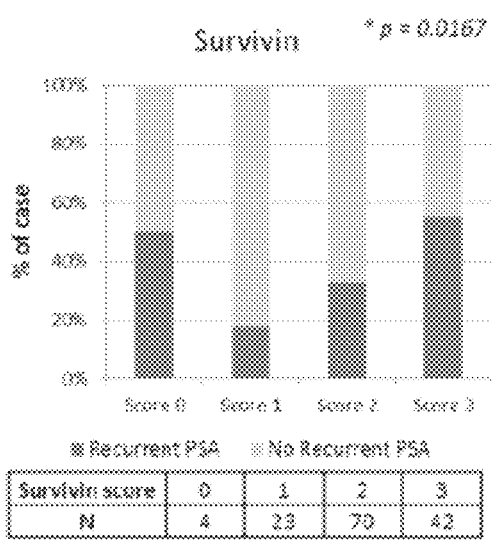
Figure 5:
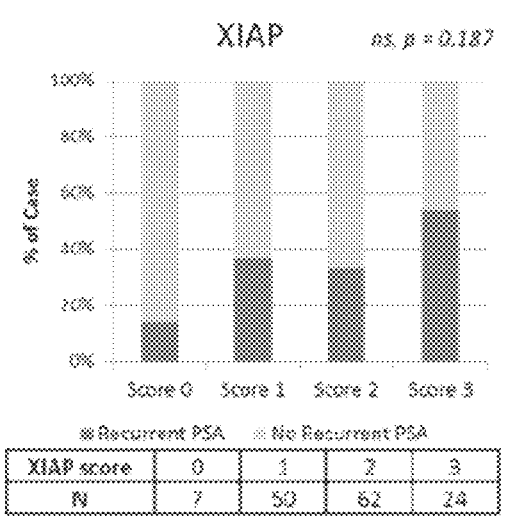
Figure 5:
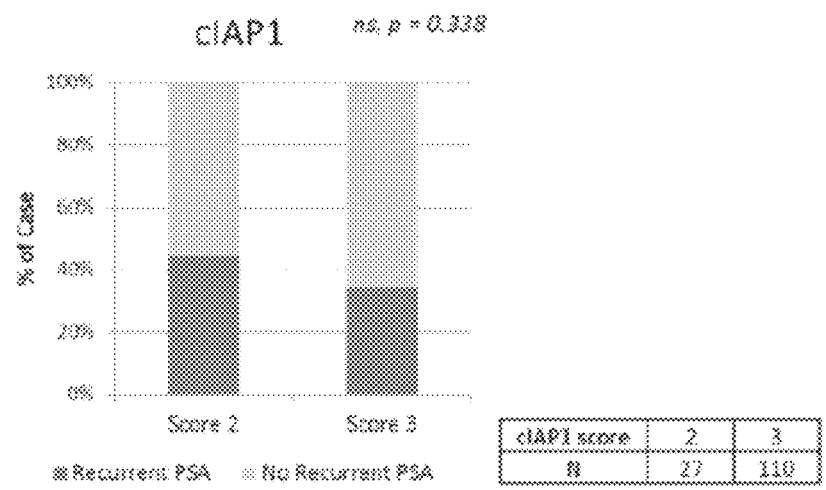
Figure 5:
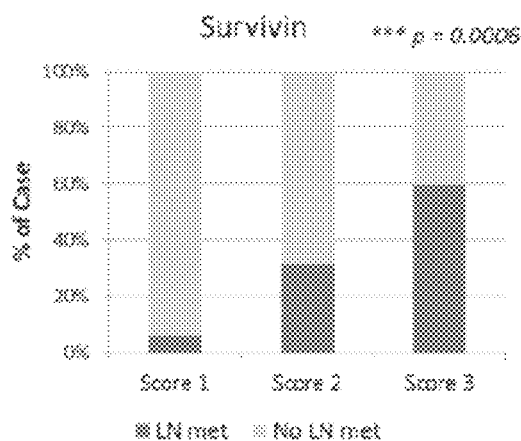
Figure 5:
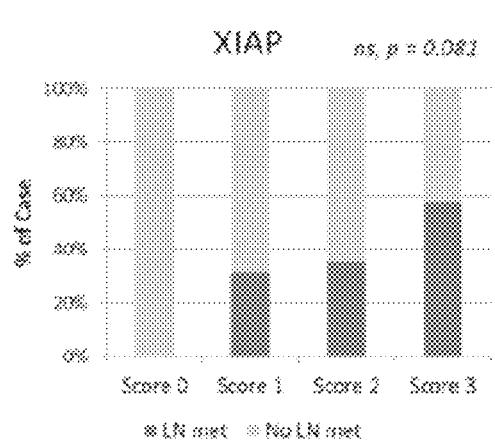
Figure 5:
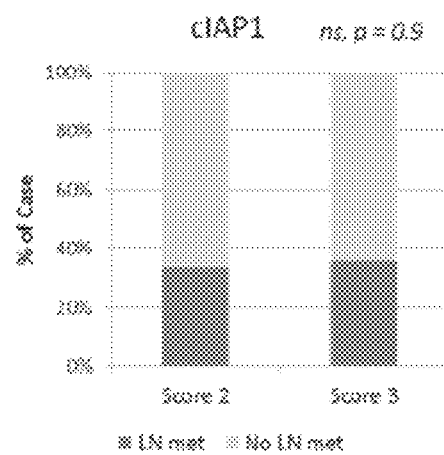

Elevated BIRC6 Protein Expression is Associated with Poor Prognostic Factors in Prostate Cancer Immunohistochemical staining of BIRC6 in prostate cancer tissue arrays revealed that BIRC6 expression was elevated in tumors at more advanced clinical stages, i.e. expression of BIRC6 was significantly higher in T3-4 stage tumors than in T1-2 stage tumors or benign prostate (mean intensity±S.E.: 1.91±0.06, 1.60±0.10 and 1.53±0.13, respectively; Benign to T3-4, p=0.0032; T1-2 to T3-4, p=0.0059; Student's t test) (FIG. 1, Panel A). Elevated BIRC6 expression also correlated positively with poor prognostic factors such as PSA recurrence (FIG. 1, Panel B), lymph node metastasis (FIG. 1, Panel C) and prostatic capsule invasion (FIG. 1, Panel D) (p=0.0571, 0.0286 and 0.0246, respectively, Chi square test for trend), indicative of its association with more advanced prostate cancer. The expression of survivin was also elevated in prostate cancer specimens (p=0.004, Benign to T3-4), and correlated similar to BIRC6 with the above poor prognostic factors (p=0.0167, PSA recurrence; p=0.028, capsule invasion; p=0.006, lymph node metastasis). Elevated XIAP expression was observed in prostate cancer and poor prognostic factors. However, statistical significance was not reached. No correlation was seen in cIAP1 (FIG. 5, Panels A-I).

Example 2

Positive Correlation between Expressions of BIRC6 and Other IAP Members in Human Prostate Cancer To establish whether there was a correlation between increases in the expression of BIRC6 in prostate cancer and those of other IAP members, the IHC expression profiles of BIRC6, XIAP, survivin and cIAP1 in individual clinical prostate samples (including benign tissue, primary cancer and CRPC) were analyzed for correlations by the Spearman's rank correlation test using GraphPad 4 software. The Spearman r coefficients for the BIRC6-survivin and BIRC6-XIAP combinations were 0.3987 and 0.6025, respectively (p<0.0001), indicating positive correlations between BIRC6 and survivin, and between BIRC6 and XIAP. A weak, but significant, positive correlation was observed for the BIRC6-cIAP1 combination, with a Spearman r coefficient of 0.194 (p=0.0072). The positive correlations between the expressions of BIRC6 and the other IAPs were visualized by representative IHC stained images of matched patients' samples (FIG. 1, Panel E).

Example 3

Figure 2:
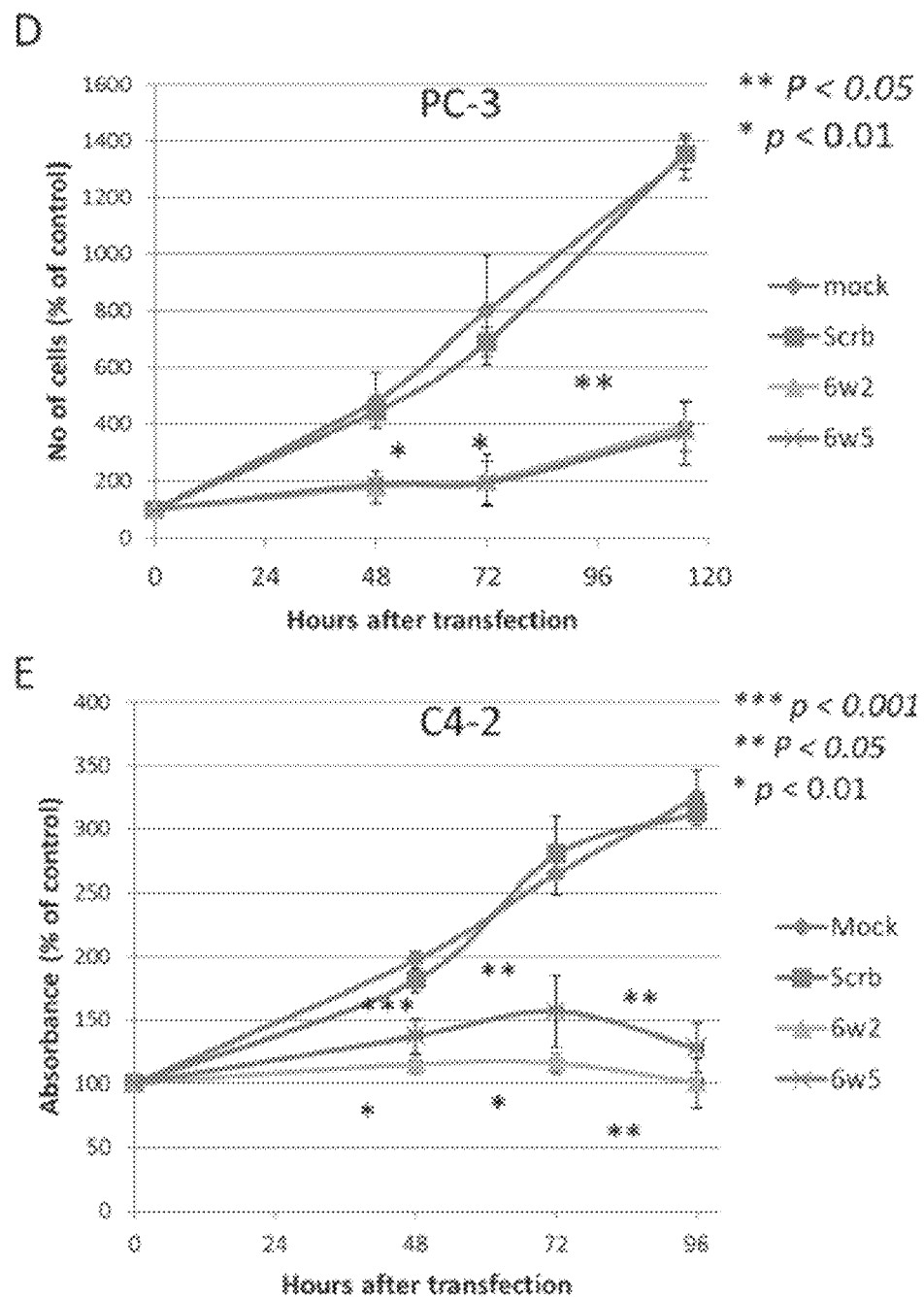
FIG. 2 shows dual IAP-targeting ASOs knockdown BIRC6, cIAP1 or survivin proteins and lead to marked suppression of CRPC cell proliferation. (A-B) show Western blotting protein levels of BIRC6, cIAP1 and survivin in two CRPC cell lines (A) PC-3 cells and (B) C4-2 cells transfected with Mock or increasing dosages of scrambled ASO (Scrb), dASOs 6w2 and 6w5 for 72 hr. (C) shows a comparison of dual IAP targeting and single IAP-targeting. Cell viability of PC-3 cells transfected with dASOs 6w2, 6w5 and siRNA-targeting BIRC6, cIAP1 or survivin, was determined by MTS assay at 72 hr after transfection. Cell viabilities of ASO- and siRNA-treated cells were normalized with corresponding Scrb ASO and siRNA controls (Error bars represent mean percentage cell viability±S.D). Western blotting of 3 IAPs showing comparable amounts of reduced protein expression obtained with dASO and siRNA single IAP-targeting. (D) shows proliferation of PC-3 cells transfected with mock, Scrb ASO, dASOs 6w2 and 6w5 (Error bars represent mean cell number±S.D). (E) shows MTS viability assay of C4-2 cells treated with dASOs.
Figure 6:
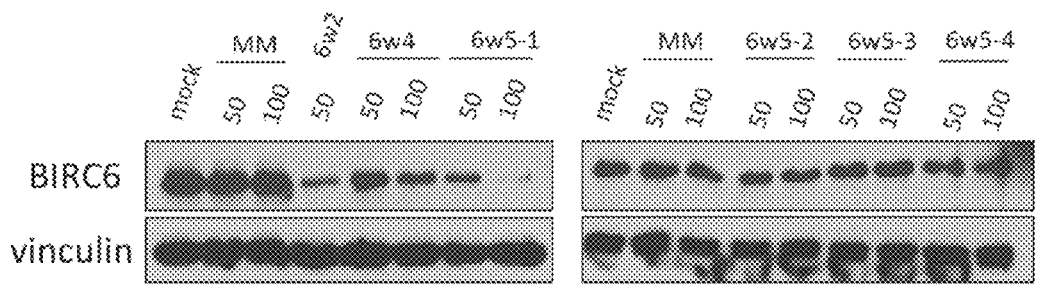
FIG. 6 shows screening of BIRC6 protein knockdown by dual-targeting ASO candidates, wherein PC3 cells were transfected with 2 doses (50 and 100 nM) of indicated dual-targeting ASOs and harvested for Western blotting analysis after 48 hr. The 6w2 and 6w5-1 dASOs in the left panel showed significant BIRC6 protein knockdown and were selected for further studies. Only the 50 nM dose of 6w2 was examined as the 100 nM treatment did not yield enough protein for assay (note: 6w5-1 is referred to as 6w5 in subsequent descriptions and MM, mismatched control).
Figure 7:
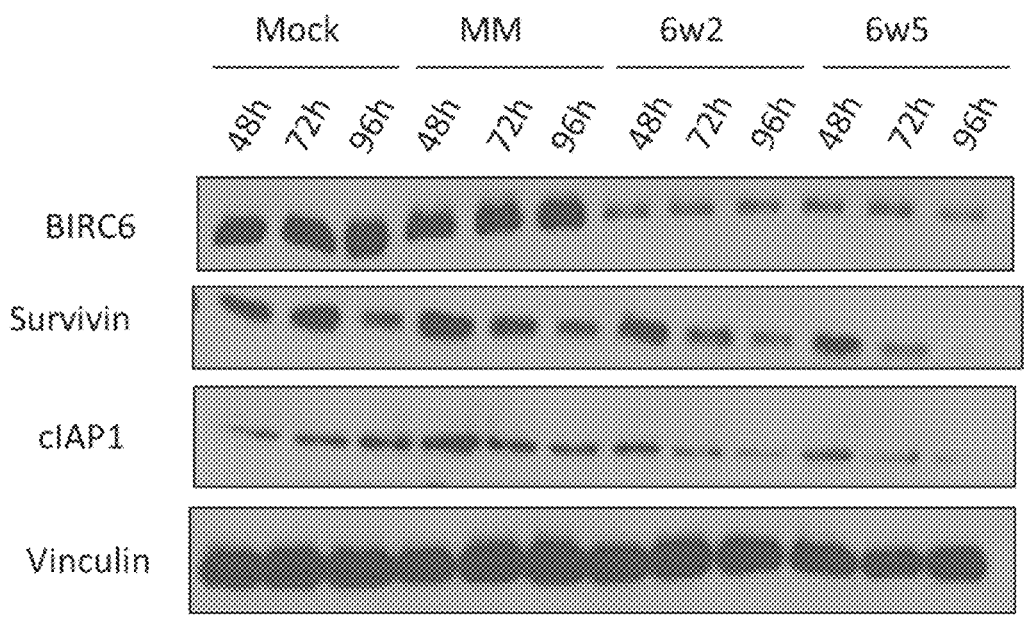
FIG. 7 shows Western blotting analysis of BIRC6, cIAP1 and survivin proteins knockdown by dASOs in time course experiment.

Dual IAP-targeting Antisense Oligonucleotides Suppress Prostate Cancer Cell Proliferation As BIRC2 (cIAP1), BIRC4 (XIAP) and BIRC5 (survivin) tended to be co-upregulated in prostate cancer in addition to BIRC6, simultaneous targeting of BIRC6 plus one of these IAP members was more likely to give superior anti-cancer effects. Accordingly, dual-targeting antisense oligonucleotides (dASOs), specifically targeting combinations of BIRC6 with each of the other three IAPs, i.e. 6w2, 6w4, 6w5, were tested for anticancer activity. As shown in Supplementary FIG. 6, only 6w2 and 6w5-1 markedly reduced BIRC6 protein levels in prostate cancer cells. The effects of these two dASOs on BIRC6, BIRC2 and BIRC5 protein levels were then tested by treating PC-3 and C4-2 cells with increasing doses of the dASOs. As shown in FIG. 2, Panels A and B, treatment with dASO 6w2 (100 and 200 nM) resulted in marked, dose-dependent reductions in both BIRC6 and cIAP1 protein expression, while dASO 6w5-1 (100 and 200 nM) (in the following text referred to as 6w5), led to marked reductions in both BIRC6 and survivin protein expressions. A time course experiment showed that treatment of PC-3 cells with dASOs 6w2 and 6w5 resulted in a marked reduction in BIRC6 protein expression after 48 hours of transfection, whereas reduction in cIAP1 and survivin protein expressions by these dASOs started at 72 hours after transfection (FIG. 7).

Example 4

The Anti-cancer Effects Obtained by Single and Dual Targeting of IAPs were Compared At a comparable degree of silencing of BIRC6, cIAP1 and survivin, knockdown of each IAP alone by siRNA did not result in marked reduction in viable PC-3 cell numbers compared to the mock control (27.8%, −20.8% and −17.7%, respectively). However, simultaneous silencing of BIRC6+cIAP1 and BIRC6+survivin by 6w2 and 6w5, respectively, led to marked reductions in the number of viable cells (49.1% and 59.8% of suppression, respectively, p<0.001). Since different silencing methodologies were used, i.e. siRNA and ASO, that presumably work via different mechanisms (Bilanges B and Stokoe D. Biochem J. 2005, 388(Pt 2):573-583), the viabilities of cells treated with either method were normalized using the cell viabilities obtained with the corresponding, non-targeting controls (FIG. 2, Panel C).

The activities of 6w2 and 6w5 were more closely examined in time course studies using cell proliferation/viability assays. Dual silencing of BIRC6+cIAP1 in PC-3 cell cultures by 6w2 effectively suppressed cell proliferation at 48, 72 and 115 hours by 77.0%, 82.4% and 76.7%, respectively, compared to Scrambled (Scrb) control (p<0.05). Similarly, silencing of BIRC6+survivin by 6w5 resulted in 74.7%, 84.1% and 78.5% growth inhibition compared to Scrb at the same time points (p<0.05) (FIG. 2, Panel D). A consistent growth-inhibitory trend was also observed using C4-2 cells and viability assays. The growth suppressions obtained with 6w2, compared to Scrb, at 48, 72 and 96 hours were 81.2% (p<0.001), 91.1% (p<0.01) and 99.9% (p<0.01), respectively, and those obtained with 6w5, compared to Scrb at 48, 72 and 96 hours were 54.0% (p<0.05), 68.3% (p<0.05) and 86.8% (p<0.01), respectively (FIG. 2, Panel E). Reductions in BIRC6 protein expression were also observed in cells treated with 100 and 200 nM scrambled ASO, but to a lower extent than obtained with the targeting ASOs. For further studies, PC-3 cells were selected due to their higher sensitivity to BIRC6 silencing.

Figure 3:
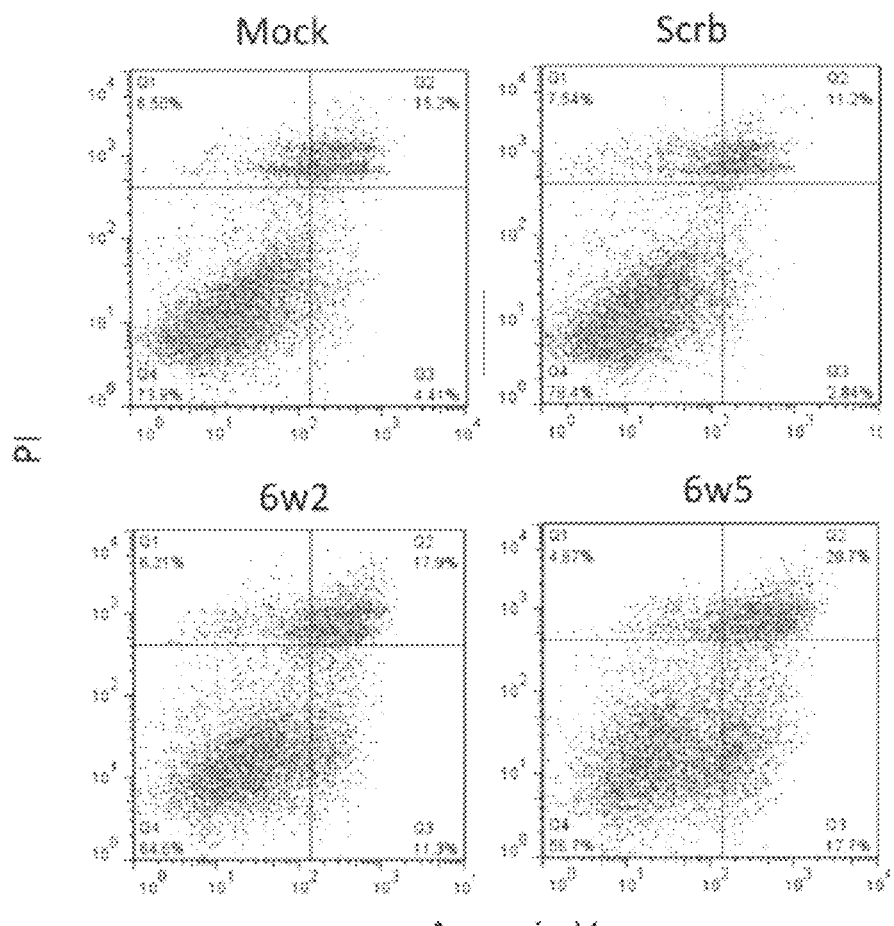
FIG. 3 shows dASOs 6w2 and 6w5 induce apoptosis, cell cycle arrest and abolish NFkB signaling. (A-B) show an Annexin V assay of PC-3 cells treated with dASOs 6w2 and 6w5 for 72 hr. (A) shows a FACS plot showing cells under early apoptosis as identified by Annexin V+, propidium iodide (PI)–. (B) shows the mean percentage of early apoptotic cells from Annexin V assay (Error bars represent mean±S.D). (C-D) show DAPI staining of dASO-treated cells. (C) shows representative images of PC-3 cells stained with DAPI after 72 hr of dASO treatment; apoptotic cells were identified by fragmented nuclei. (D) shows quantification of cells undergoing apoptosis: percentage of fragmented nuclei. (E) shows cell cycle distribution of PC-3 cells treated with ASOs for 72 hr as determined by PI staining. (F) shows percentage of cells at the G2-M phase. (G) shows NFkB transcription activation was examined using a NFkB dual luciferase reporter assay. PC-3 cells were co-transfected with dASOs, NFkB-responsive firefly luciferase and Renilla luciferase plasmid. Luciferase activity was measured at 48 hr after transfection with prior induction by TNF-α treatment.
Figure 3:
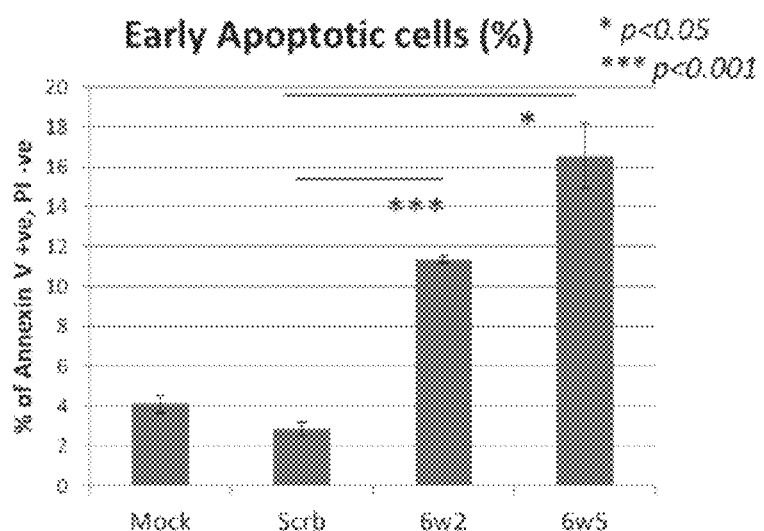
Figure 3:
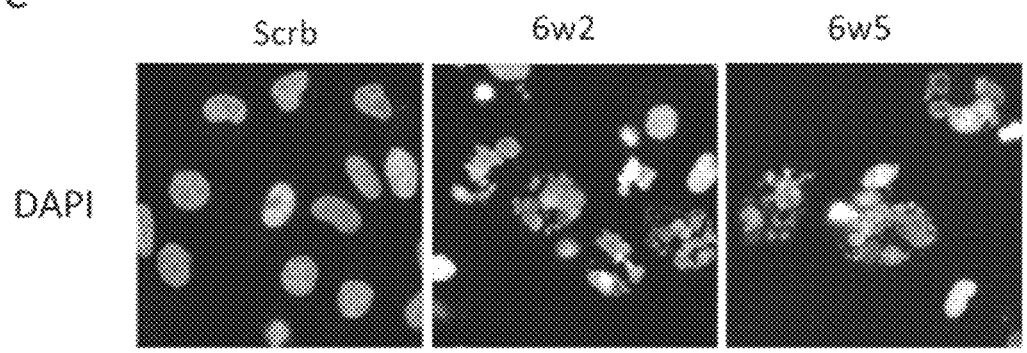
Figure 3:
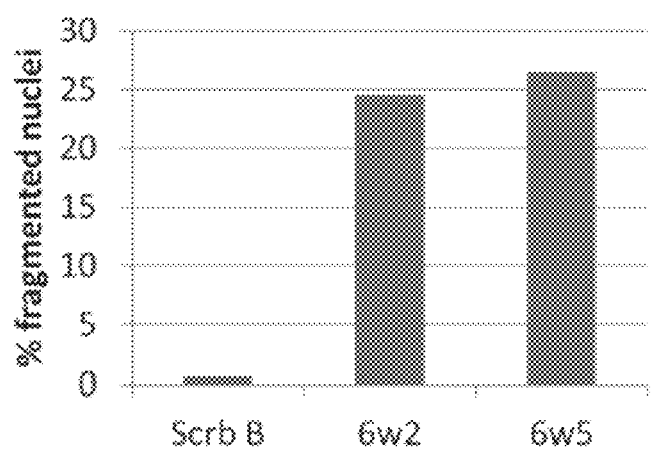
Figure 3:
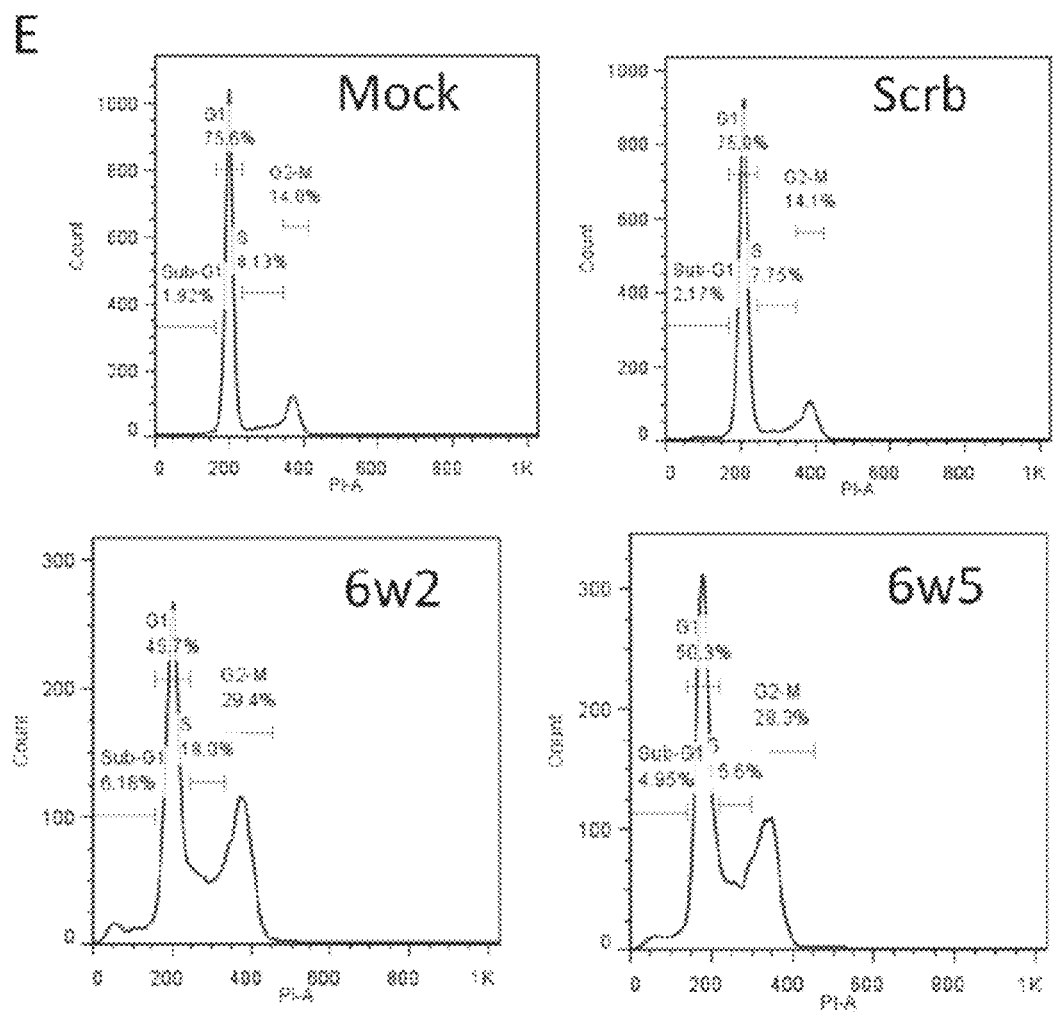
Figure 3:
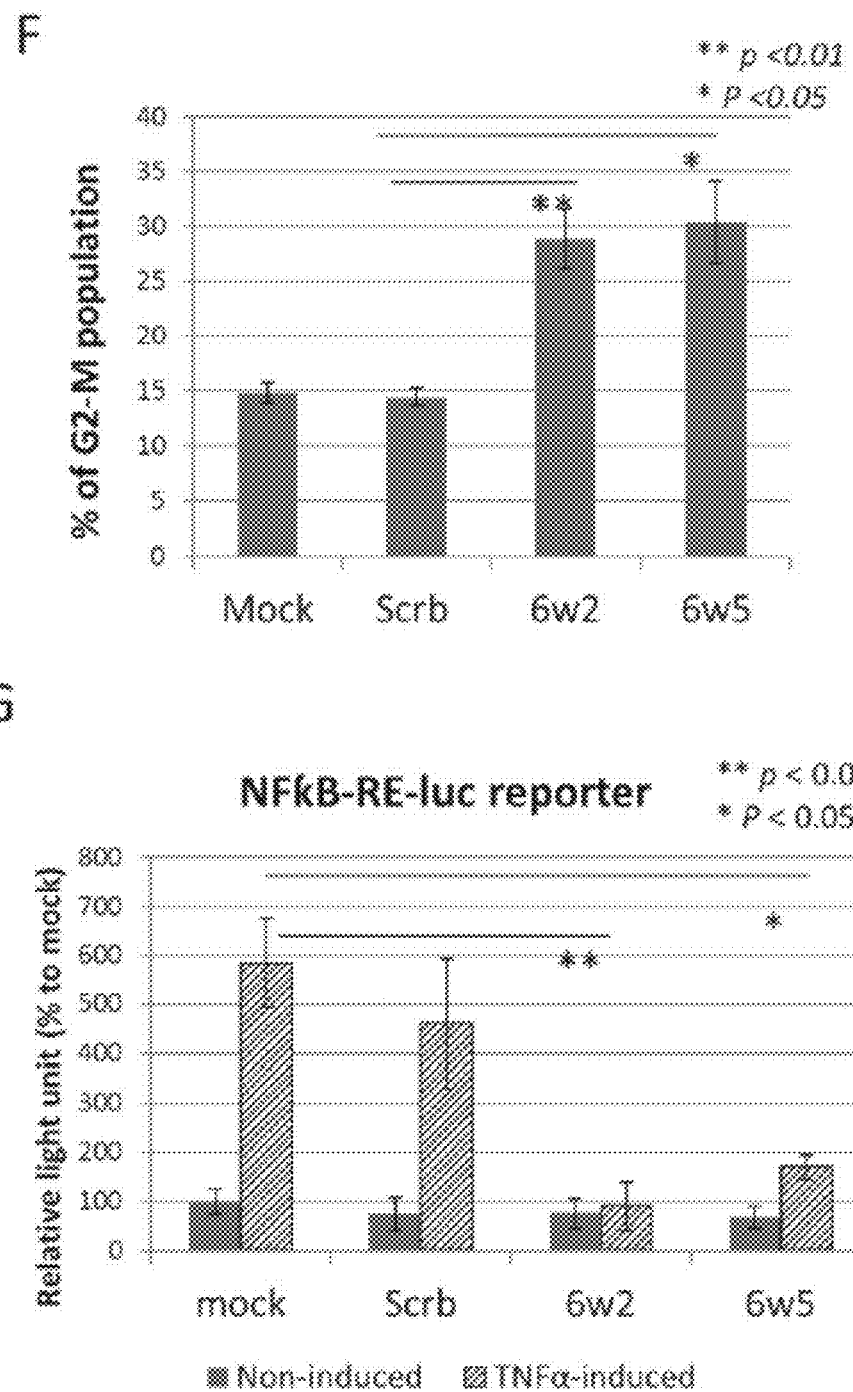

Example 5 dASOs 6w2 and 6w5 Induce Apoptosis, Cell Cycle Arrest and Suppress NFkB Activation To understand the cause of growth-inhibition given by dASOs, apoptosis induction was first investigated. PC-3 cells were incubated with dASOs 6w2 and 6w5 for 72 hours and then subjected to Annexin V and PI staining and FACS analysis to determine the amount of early apoptotic cells generated. FACS analysis showed that the treatments led to apoptosis of 11.3% and 16.6% obtained with 6w2 and 6w5, respectively, compared to 2.8% obtained with Scrb ASO (p=6.68×10-5 and 0.047 respectively) (FIG. 3, Panels A, B). In addition, PC-3 cells treated with dASOs 6w2 and 6w5 for 72 hours were stained with DAPI and the numbers of fragmented nuclei (a key indicator of apoptosis), were determined under a fluorescent microscope. The percentage of cells containing apoptotic nuclei was 24.6% and 26.5% for 6w2- and 6w5-treated cells, respectively, in contrast to 0.64% for Scrb ASO-treated cells (FIG. 3, Panels C, D). FACS analysis of PI-stained PC-3 cells showed that dASO 6w2 and 6w5 treatments were associated with significant increases in the G2-M phase population [28.9% for 6w2 (p=0.008) and 30.4% for 6w5 (p=0.015)], compared to the Scrb control (14.4%) and mock control (14.8%) (FIG. 3, Panels E, F). Increases in S phase population were also observed in both treated groups.

Figure 8:
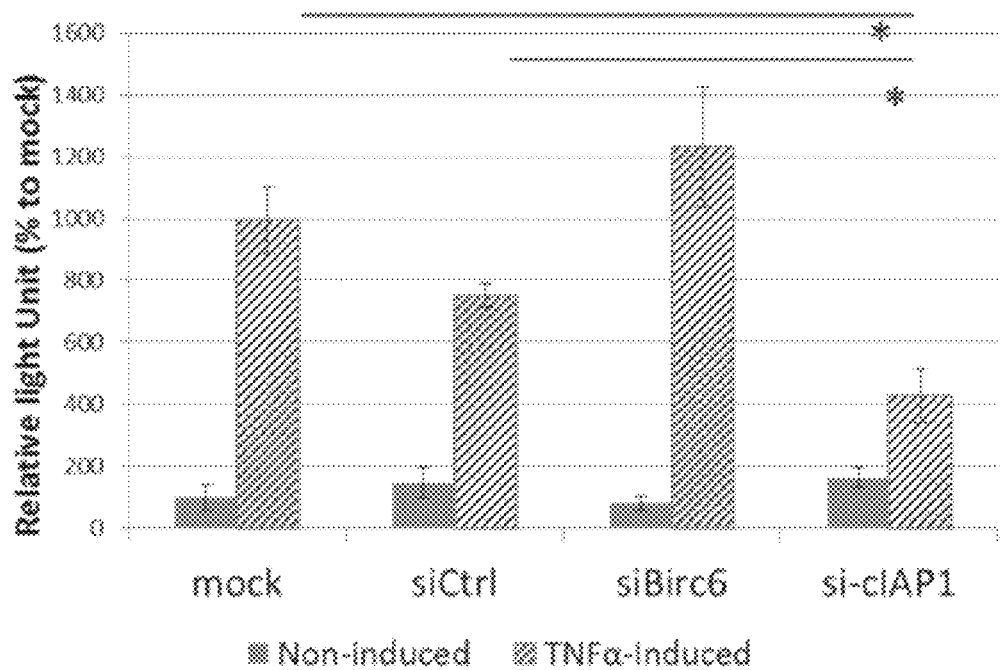
FIG. 8 shows silencing of BIRC6 alone did not affect TNF-α induced NFkB transcription activation.

In view of a close link between IAPs and the NFkB pathway (Krieg A, et al., Proc Natl Acad Sci USA. 2009; 106(34):14524-14529; Varfolomeev E, et al., J Biol Chem. 2008, 283(36):24295-24299), the effects of dASO 6w2 and 6w5 on NFkB transactivation in PC-3 cells were examined using a dual luciferase reporter assay under TNFα-induced and non-induced conditions. The TNFα-induced NFkB activation was markedly suppressed in dASO 6w2-treated cells compared to cells treated with Mock (97.0%, % suppression to mock, p=0.003), whereas NFkB activation was 20.2% suppressed by Scrb ASO compared to Mock. A marked suppression of NFkB activation was also observed in dASO 6w5-treated cells (79.0%, % of suppression to mock, p=0.011) (FIG. 3, Panel G). Furthermore, siRNA silencing of BIRC6 did not reduce TNFα-induced NFkB activation, in contrast to silencing of cIAP1 (p=0.029 and 0.012 to Mock and siCtrl respectively), indicating that the dASO-induced inhibition of NFkB transactivation was not caused by BIRC6 alone (FIG. 8).

Taken together, the results demonstrate that the growth suppression of dASO 6w2- and 6w5-treated PC-3 cells was associated with apoptosis induction, G2-M phase arrest and repression of NFkB promoter activation, highlighting the multifaceted action of both dASOs. dASOs suppress PC-3 xenograft growth.

Example 6

The Therapeutic Potential of dASOs was Examined In Vivo

Figure 4:
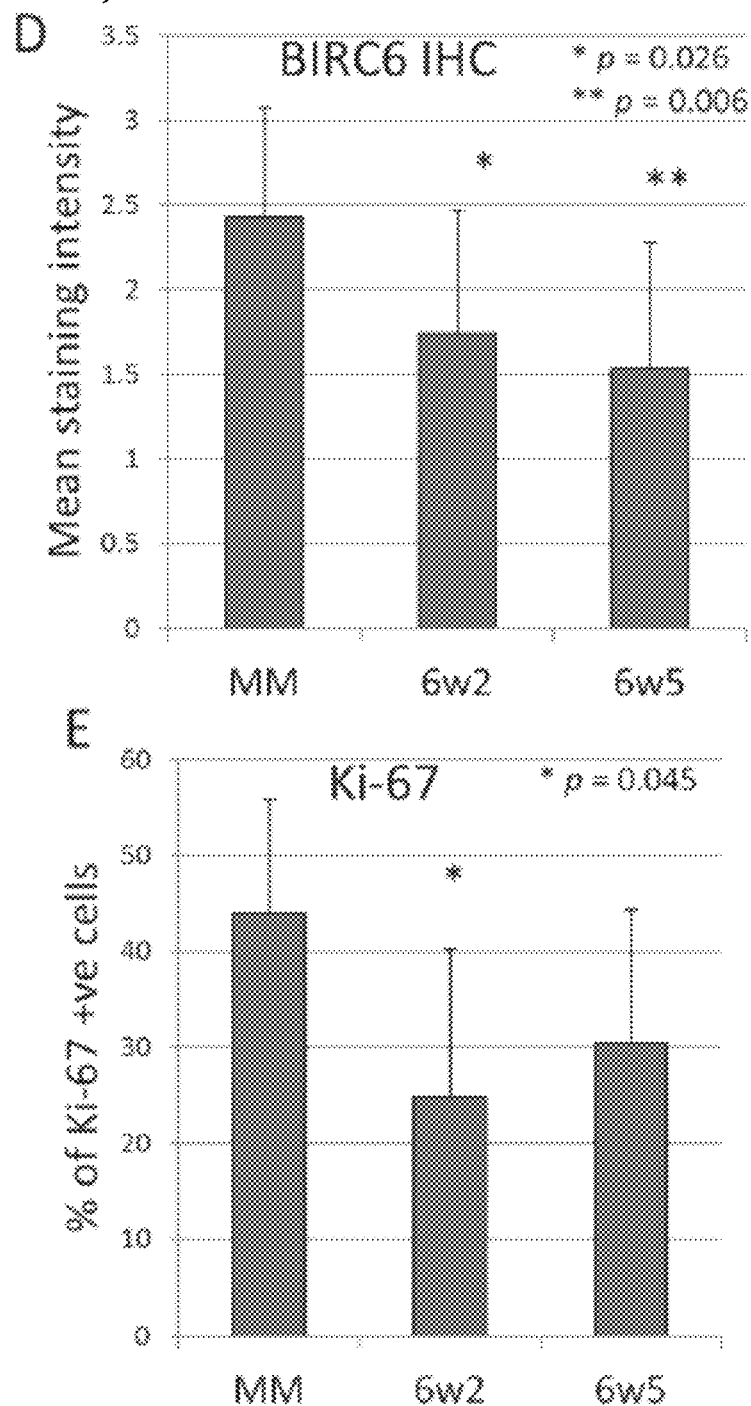
FIG. 4 shows treatments with dASOs resulted in significant lower viable tumor volume. (A) shows total tumor volumes at the end of treatment (day 15) in NOD-SCID mice with established PC-3 subcutaneous xenografts when treated with control, 6w2 and 6w5 dASOs for 15 consecutive days. (B) shows percent tumor necrosis at the end of treatment (day 15) in NOD-SCID mice with established PC-3 subcutaneous xenografts when treated with control, 6w2 and 6w5 dASOs for 15 consecutive days. (C) shows percent viable tumor volume as compared to control at the end of treatment (day 15) in NOD-SCID mice with established PC-3 subcutaneous xenografts when treated with control, 6w2 and 6w5 dASOs for 15 consecutive days. (D and E) show mean staining intensity for BIRC6 IHC and percent of Ki-67 positive cells, respectively. (F) shows cell micrographs stained with Hematoxylin and eosin stain (H&E) or antibodies for BIRC6, cleaved caspase 3 and Ki-67, to compare cells that have been treated with control (MM), with 6w2 dASO and 6w5 dASO treated cells.
Figure 4:
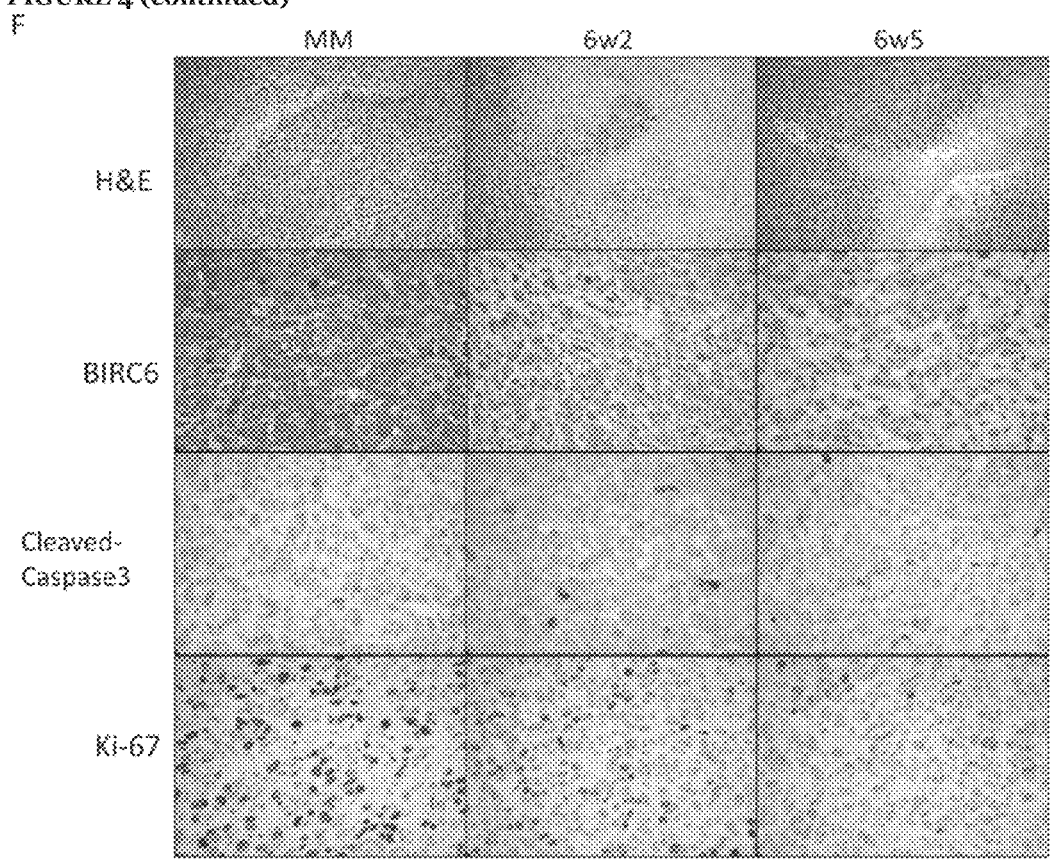

NOD-SCID mice carrying subcutaneous PC-3 xenografts were treated daily for 15 days with dASOs 6w2, 6w5 or mismatched (MM) ASO (10 mg/kg). Tumor volumes were determined at the end of the treatment; there was no significant difference in total volume between tumors in control and treatment groups (FIG. 4, Panel A). However, as revealed by H&E staining, tumors in the dASO-treated groups were found to contain a significantly higher percentage of tumor necrosis compared to the control group (46.67%±7.86 and 46.25%±8.17% of necrotic area for 6w2 and 6w5 compared to 19.33%±9.49 in control; mean % of necrotic area±S.E.M, FIG. 4, Panel B). To estimate the viable tumor volume, we used the calculation: total tumour volume×(100%−% of necrotic area). As shown in FIG. 4, Panel C, mice treated with dASOs 6w2 and 6w5 showed significantly lower viable tumor volume, with percentage of viable tumor volume to control of 61.69%±9.30, p=0.0139 and 58.56%±9.14, p =0.0078 respectively.

Figure 9:
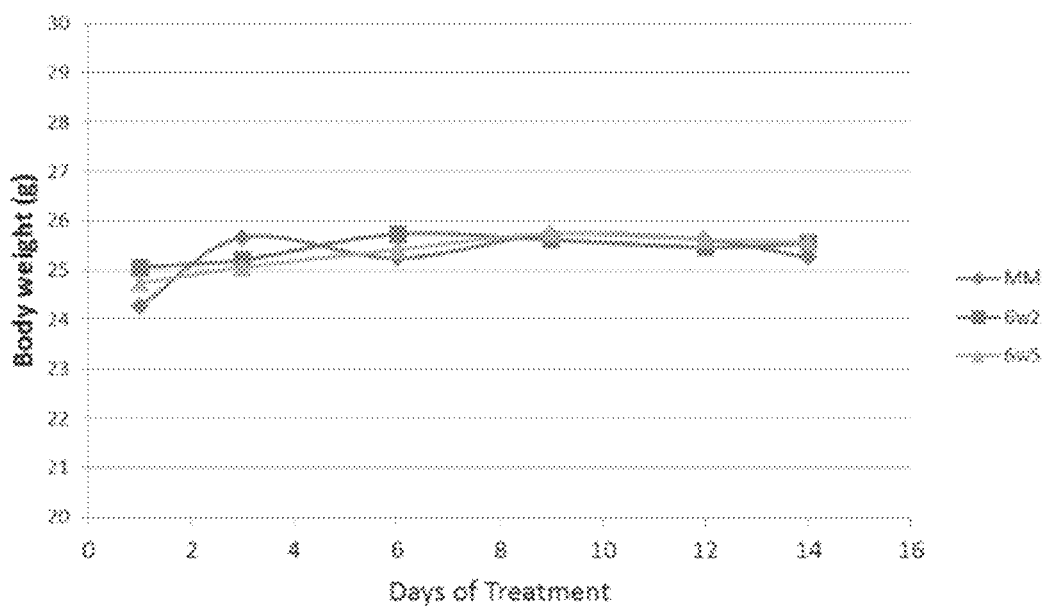
FIG. 9 shows treatment with the dASOs did not affect the weights of the mice.
Figure 10:
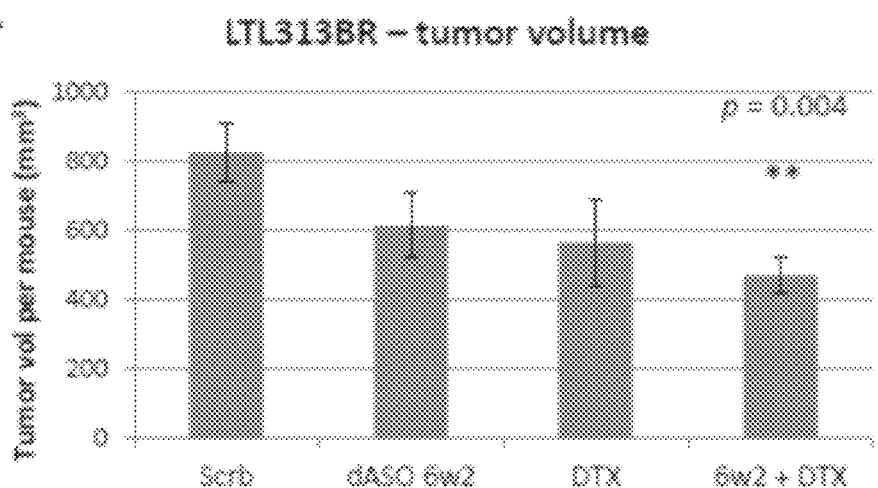
FIG. 10 shows dASO 6w2 in combination with docetaxel significantly suppresses CRPC patient derived xenograft model LTL313BR. (A) shows NOD-SCID mice with established castration resistant xenografts were treated with scramble control (Scrb), 6w2, docetaxel (DTX) and combination of 6w2 and DTX, for 15 days (5-day on, 2-day off), wherein tumour volumes were measured at the end of treatment (mean+S.E.M—where two pieces of tumor were subrenal grafted per mouse, one tumor per kidney). (B) shows treatment of 6w2, DTX and 6w2+DTX reduced serum PSA levels compared to Scrb control from day 10 to end of treatment at day 19.
Figure 10:
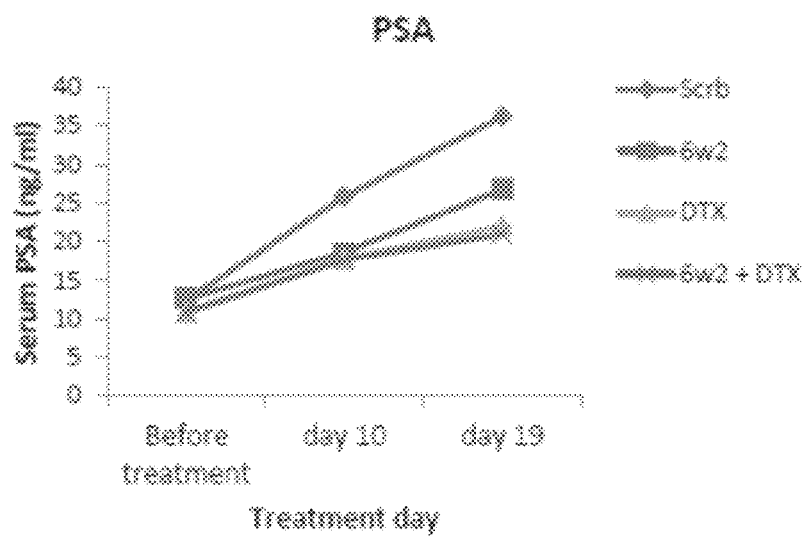

The dASO-reduced tumor growth was associated with a significant decrease in intratumoral BIRC6 protein expression in both treatment groups compared to the MM control (p=0.026 for MM to 6w2, p=0.006 for MM to 6w5) (FIG. 4, Panel D). However, no discernable reduction in the secondary target levels via IHC staining, cIAP1 and survivin, was detected in the tumours under the current treatment regimen. Ki-67 staining showed that the suppressed tumour growth was associated with a significant decrease in the number of proliferating cells in 6w2 treated group (p=0.045). 6w5 treatment was also associated with reduction of proliferating cells although statistical significance was not reached (FIG. 4, Panels D and E). No significant increase in cleaved caspase-3 expression was observed in the dASO-treated tumours at harvest (FIG. 4, Panel F). The treatment with the dASOs did not induce host toxicity as the weights of the mice were not significantly affected during the course of the treatment (FIG. 9). Furthermore, the treated tumors looked pallid compared to the untreated tumors (data not shown). Taken together, the results indicate that treatment with dASOs 6w2 and 6w5 suppressed PC-3 tumor growth in vivo without major toxicity to the host.

Example 7

Figure 11:
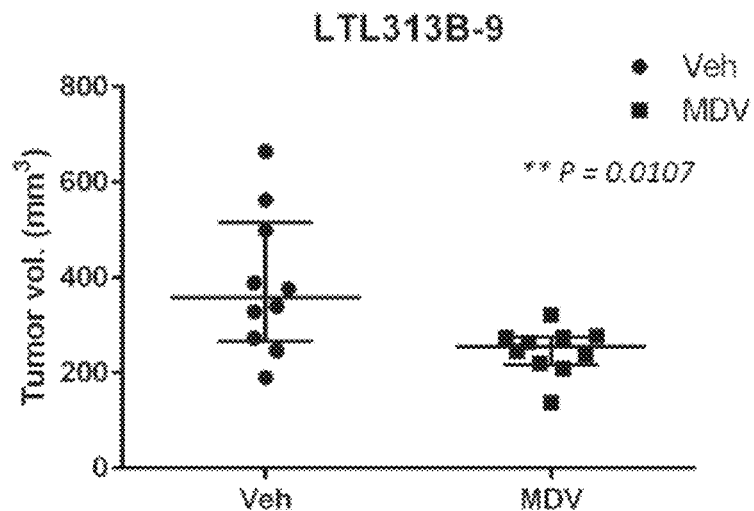
FIG. 11 shows patient derived xenograft (PDX) model LTL313BR as a clinically relevant model for enzalutamide (ENZ) resistant CRPC. (A/B) show mice bearing subrenal grafted LTL313B or LTL313BR tumors when treated with 10 mg/kg enzalutamide (MDV or ENZ) or vehicle for 4 weeks. Tumors were harvested and tumor volume was measured at the end of treatment. LTL313B parental line was sensitive to enzalutamide treatment (A) but not for the CRPC line LTL313BR (B).
Figure 11:
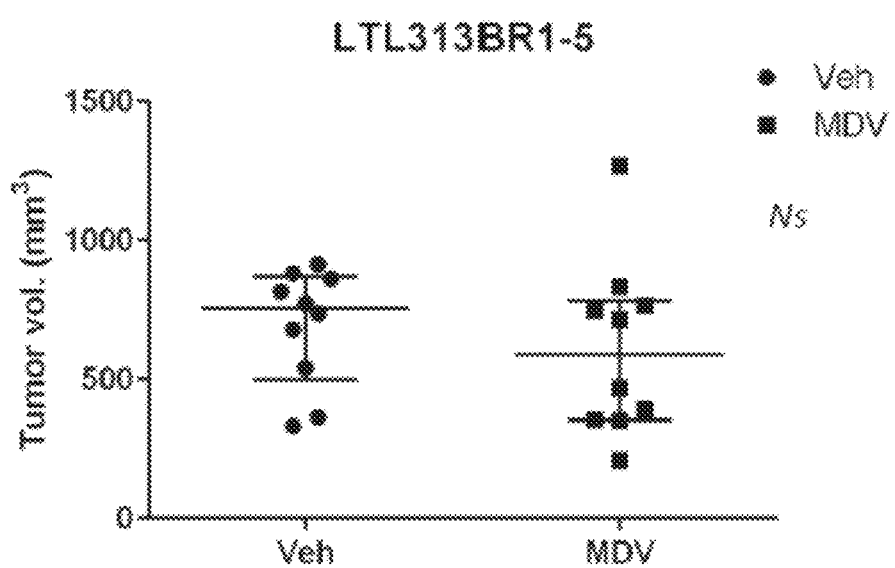

Patient Derived Xenograft Model LTL313BR as a Clinically Relevant Model for Enzalutamide (ENZ) Resistant CRPC In order to search for PDX models for ENZ-CRPC, a panel of 8 PDX tumor lines were treated with ENZ (10 mg/kg ENZ or vehicle for 4 weeks, N=10 per group) and their responses to ENZ in terms of tumor growth were examined at the end of treatment. Among the panel, LTL313BR CRPC line did not respond to ENZ treatment whereas its parental line LTL313B readily responded to ENZ treatment (FIG. 11). To our knowledge, LTL313BR is the first-in-field PDX model for ENZ-resistant CRPC.

Example 8

Enzalutamide Resistant Phenotype was Associated with Elevated BIRC6 Expression

Figure 12:
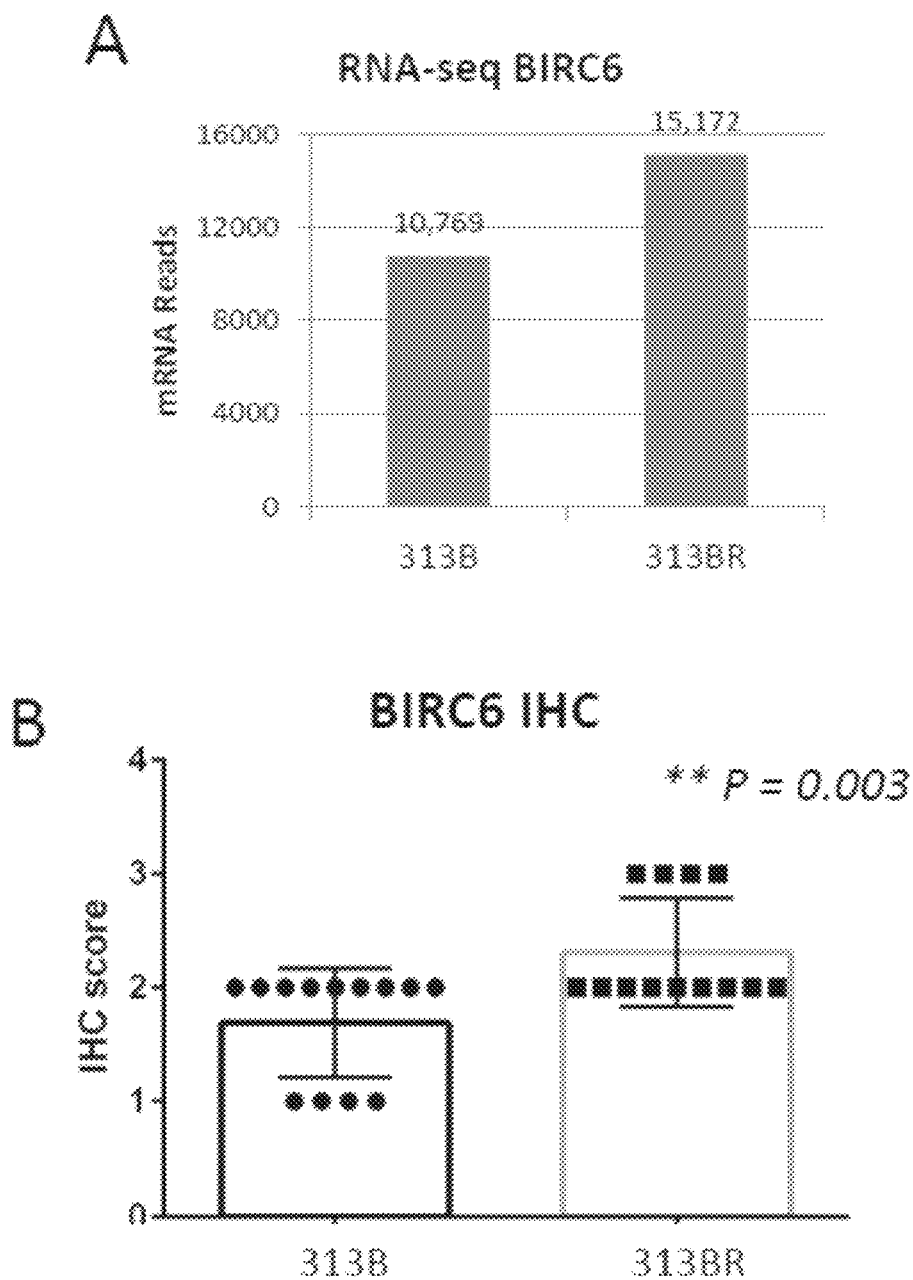
FIG. 12 shows ENZ resistant phenotype was associated with elevated BIRC6 expression. (A-C) shows BIRC6 was elevated in ENZ-resistant 313BR over ENZ-responding 313B at both mRNA and protein levels as demonstrated by RNA-seq and immunohistochemistry respectively (Magnification, 400×). (D) shows an upregulation trend of BIRC6 protein was observed in 313BR tumors treated with enzalutamide versus vehicle control. IHC scores 0, 1, 2, 3 refer to negative, weak, mild and strong staining intensities respectively.
Figure 12:
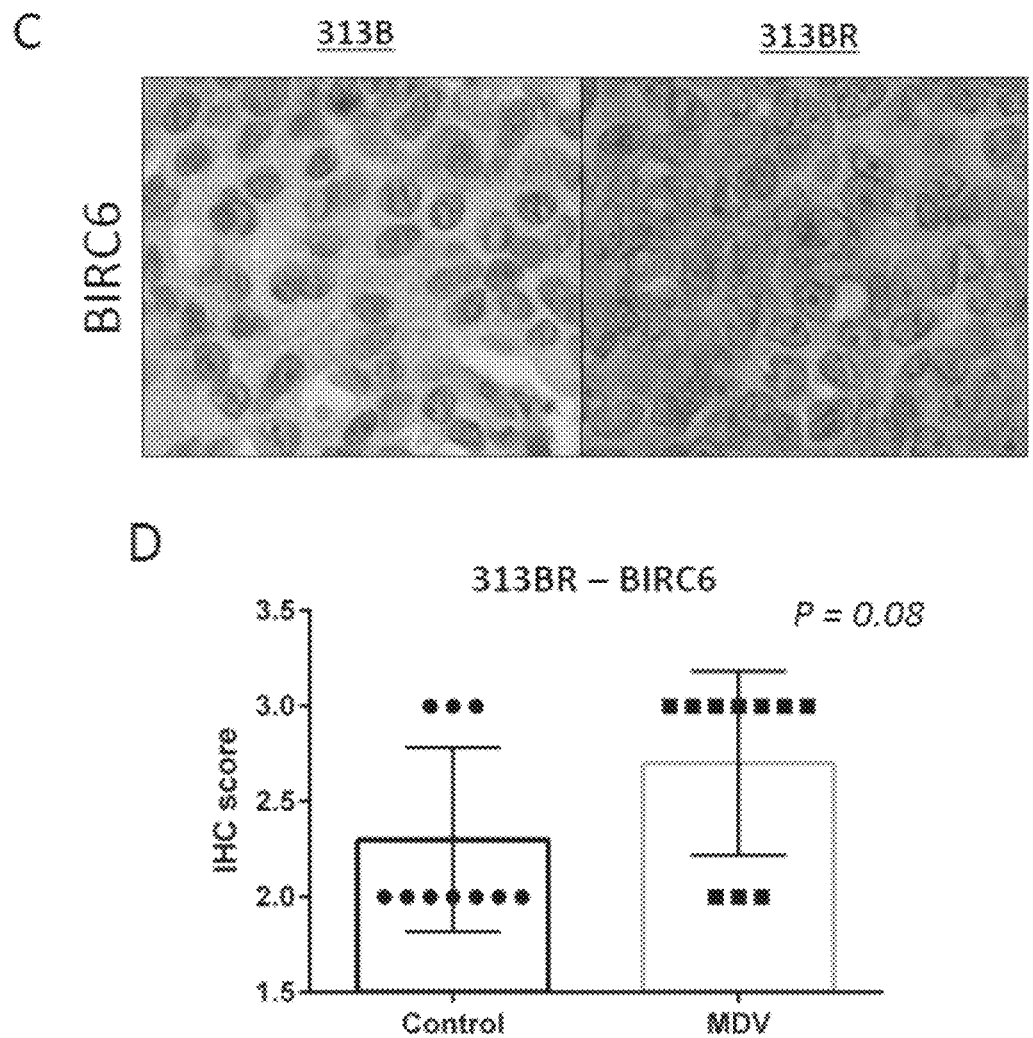

BIRC6 is reported for its role in promoting treatment resistance; however, its association with ENZ resistance is unknown. Here, we compared BIRC6 mRNA and protein expression between LTL313B and LTL313BR by RNA-seq and immunohistochemistry. BIRC6 was elevated in LTL313BR for both mRNA and protein levels. In addition, an upregulation trend of BIRC6 protein was also observed in ENZ treated LTL313BR tumors compared with vehicle control (FIG. 12).

Example 9

6w2 Effectively Suppressed Enz-resistant LTL313BR Growth

Figure 13:
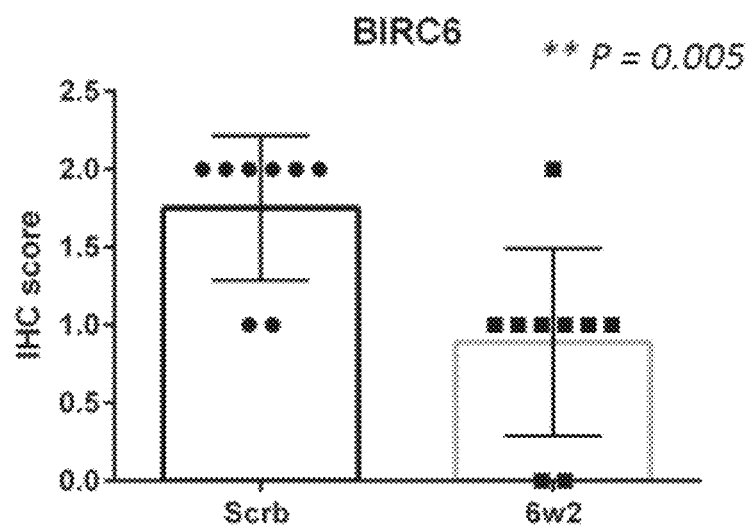
FIG. 13 shows that in vivo treatment with dASO 6w2 significantly suppressed LTL313BR BIRC6. Mice were treated with scrambled (Scrb) or 6w2 dASOs for 15 days and tumors were harvested at the end of treatment (A/B). BIRC6 expression was significantly suppressed as evident from immunohistochemistry staining.
Figure 13:
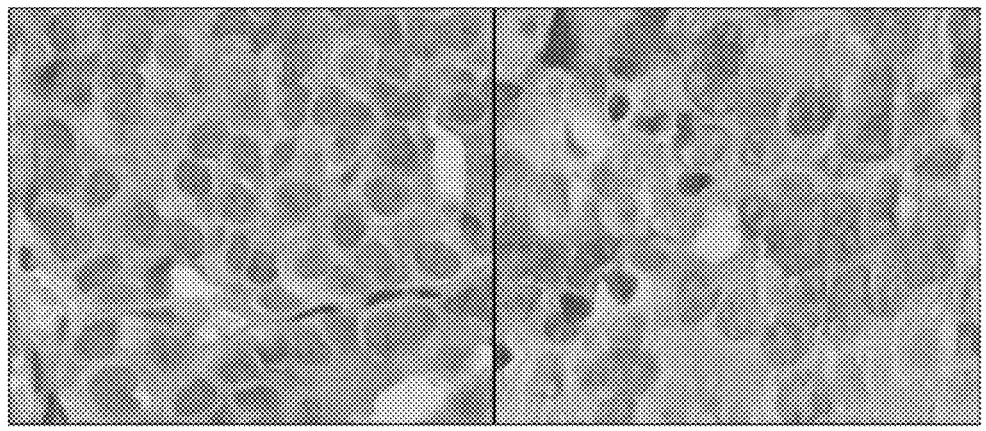
Figure 14:
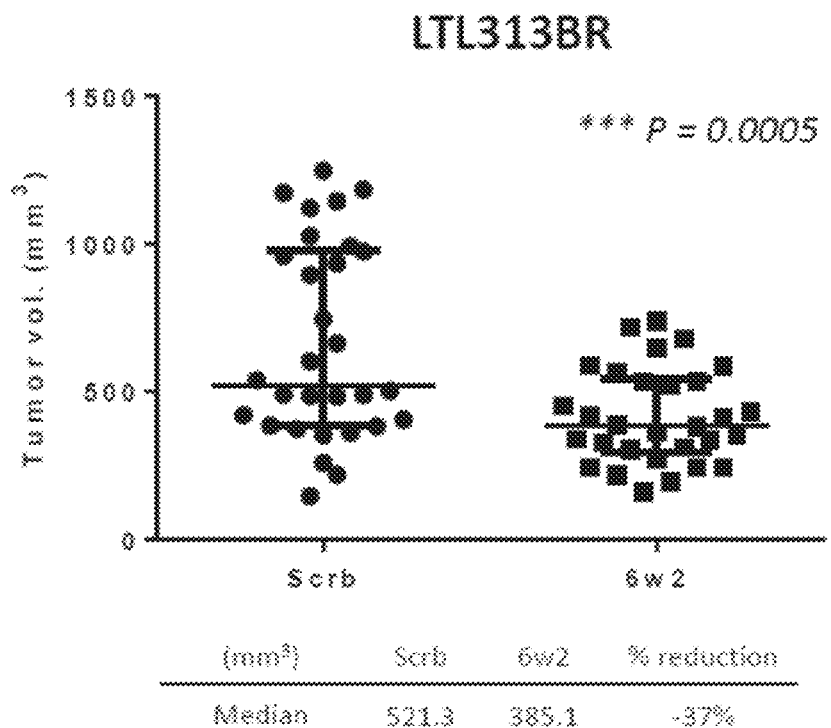
FIG. 14 shows dASO 6w2 effectively suppressed Enz-resistant LTL313BR growth. Mice bearing enzalutamide resistant LTL313BR line were treated with scrambled control or 6w2 dASO daily for 21 days. Tumors were harvested 1 week after the end of treatment. (A) 6w2 treated group resulted in significantly smaller tumor volume than scrb treated group (37% smaller in median tumor volume). (B) Increase of serum PSA levels from beginning of treatment to harvest (in 4-week period) of 6w2 treated mice were also significantly lower than scrb control (39% lower). Whisker=median/mean±interquartile range.
Figure 14:
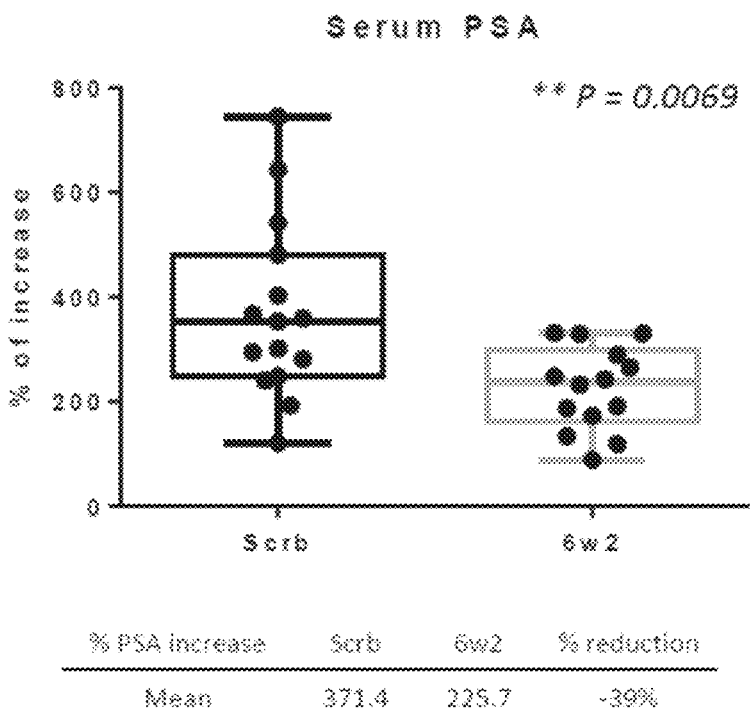

BIRC6 target inhibition was first validated in pilot set LTL313BR (n=8 for scrambled control and n=9 for 6w2) by IHC staining (FIG. 13). Anti-tumor efficacy of 6w2 ASO towards ENZ-resistant CRPC was then studied in a larger cohort (n=30 per group). Mice bearing LTL313BR tumors were treated with scrb or 6w2 dASO daily for 21 days and tumors were harvested 1 week after the end of treatment (FIG. 14, Panel A). 6w2 treated group showed significantly smaller tumors than scrb control group (37% smaller in median tumor volume, FIG. 14, Panel B) as well as significant reduction of serum PSA increase (FIG. 14, Panel C).

Example 10

Figure 15:
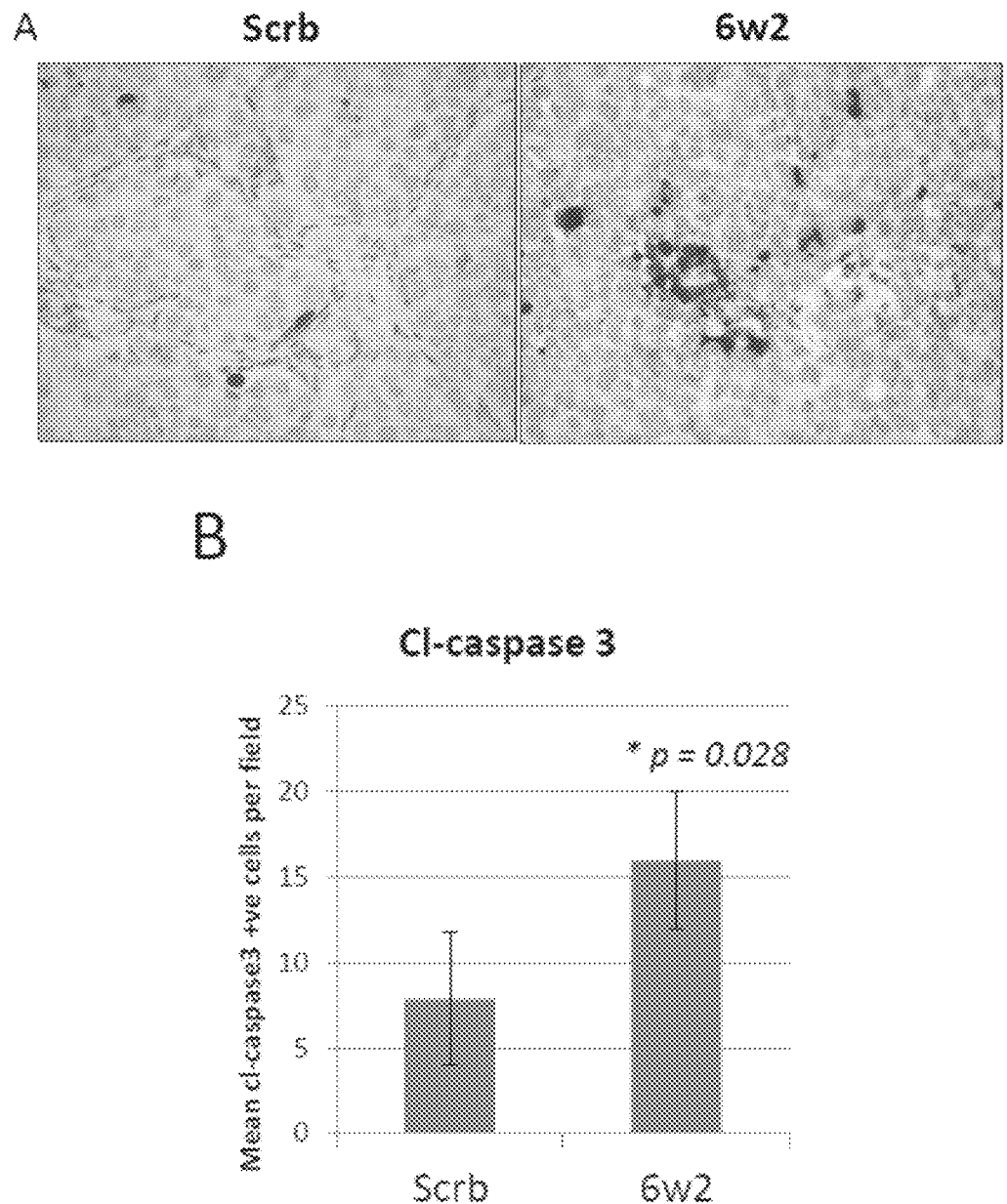
FIG. 15 shows dASO 6w2 treatment increased apoptosis of LTL313BR. 6w2 treated group showed significant increase in apoptotic cells. Representative images of immunohistochemistry staining showing positive staining of cleaved caspase 3 in (A). The number of positively stained cells were quantified in 3 to 5 fields (400× magnification) per sample are shown in (B). Error bars=mean±S.D.

6w2 Treatment Simultaneously Increased Apoptosis and Suppressed Pro-survival Factors in LTL313BR Tumors To understand the underlying cause of inhibitory effect induced by 6w2, we first examined the presence of apoptosis induction by IHC cleaved caspase-3 staining. 6w2 treated tumors demonstrated 2-fold increase of percentage of apoptotic cells (16%) compared to that of scrb (7.5%) (FIG. 15). Moreover, 6w2 treatment was associated with reduced mRNA expressions of factors in CRPC prosurvival signaling, including androgen receptor and TMPRSS2 in androgen receptor signaling, RANK and BCL2 in NFkB signaling, and IGFBP5 in IGFR signaling (FIG. 16).

The above ENZ-resistant CRPC PDX model results, suggest that dASO 6w2 harbours significant therapeutic effect towards ENZ-resistant CRPC. As such, dASO 6w2 may represent an effective therapeutic option for the emerging ENZ-resistant CRPC incidence in clinic.

Although embodiments described herein have been described in some detail by way of illustration and example for the purposes of clarity of understanding, it will be readily apparent to those of skill in the art in light of the teachings described herein that changes and modifications may be made thereto without departing from the spirit or scope of the appended claims. Such modifications include the substitution of known equivalents for any aspect of the invention in order to achieve the same result in substantially the same way. Numeric ranges are inclusive of the numbers defining the range. The word "comprising" is used herein as an open ended term, substantially equivalent to the phrase "including, but not limited to", and the word "comprises" has a corresponding meaning. As used herein, the singular forms "a", "an" and "the" include plural referents unless the context clearly dictates otherwise. Thus, for example, reference to "a thing" includes more than one such thing. Citation of references herein is not an admission that such references are prior art to an embodiment of the present invention. The invention includes all embodiments and variations substantially as herein described and with reference to the figures.

REFERENCES

Arnt C R, Chiorean M V, Heldebrant M P, Gores G J and Kaufmann S H. Synthetic Smac/DIABLO peptides enhance the effects of chemotherapeutic agents by binding XIAP and cIAP1 in situ. J Biol Chem. 2002; 277(46):44236-44243.

Bartke T, Pohl C, Pyrowolakis G and Jentsch S. Dual role of BRUCE as an antiapoptotic IAP and a chimeric E2/E3 ubiquitin ligase. Mol Cell. 2004; 14(6):801-811.

Bianchini M, Levy E, Zucchini C, Pinski V, Macagno C, De Sanctis P, Valvassori L, Carinci P and Mordoh J. Comparative study of gene expression by cDNA microarray in human colorectal cancer tissues and normal mucosa. Int J Oncol. 2006; 29(1):83-94.

Bilanges B and Stokoe D. Direct comparison of the specificity of gene silencing using antisense oligonucleotides and RNAi. Biochem J. 2005; 388(Pt 2):573-583.

Bishr M and Saad F. Overview of the latest treatments for castration-resistant prostate cancer. Nat Rev Urol. 2013; 10(9):522-528.

Carrasco R A, Stamm N B, Marcusson E, Sandusky G, Iversen P and Patel B K. Antisense inhibition of survivin expression as a cancer therapeutic. Mol Cancer Ther. 2011; 10(2):221-232.

Chen Z, Naito M, Hori S, Mashima T, Yamori T and Tsuruo T. A human IAP-family gene, apollon, expressed in human brain cancer cells. Biochem Biophys Res Commun. 1999; 264(3):847-854.

Cheung H, Plenchette S, Kern C J, Mahoney D J and Korneluk R G. The RING domain of cIAP1 mediates the degradation of RING-bearing inhibitor of apoptosis proteins by distinct pathways. Mol Biol Cell. 2008; 19(7):2729-2740.

Chu L, Gu J, Sun L, Qian Q, Qian C and Liu X. Oncolytic adenovirus-mediated shRNA against Apollon inhibits tumor cell growth and enhances antitumor effect of 5-fluorouracil. Gene Ther. 2008; 15(7):484-494.

Claessens F, Helsen C, Prekovic S, Van den Broeck T, Spans L, Van Poppel H and Joniau S. Emerging mechanisms of enzalutamide resistance in prostate cancer. Nat Rev Urol. 2014; 11(12):712-716.

Dai Y, Liu M, Tang W, DeSano J, Burstein E, Davis M, Pienta K, Lawrence T and Xu L. Molecularly targeted radiosensitization of human prostate cancer by modulating inhibitor of apoptosis. Clin Cancer Res. 2008; 14(23):7701-7710.

de Almagro M C and Vucic D. The inhibitor of apoptosis (IAP) proteins are critical regulators of signaling pathways and targets for anti-cancer therapy. Exp Oncol. 2012; 34(3):200-211.

Dias N and Stein C A. Antisense oligonucleotides: basic concepts and mechanisms. Mol Cancer Ther. 2002; 1(5):347-355.

Dong X, Lin D, Low C, Vucic E A, English J C, Yee J, Murray N, Lam W L, Ling V, Lam S, Gout P W and Wang Y. Elevated expression of BIRC6 protein in non-small-cell lung cancers is associated with cancer recurrence and chemoresistance. J Thorac Oncol. 2013; 8(2):161-170.

Fulda S, Wick W, Weller M and Debatin K M. Smac agonists sensitize for Apo2L/TRAIL- or anticancer drug-induced apoptosis and induce regression of malignant glioma in vivo. Nat Med. 2002; 8(8):808-815.

Gleave M, Miyake H and Chi K. Beyond simple castration: targeting the molecular basis of treatment resistance in advanced prostate cancer. Cancer Chemother Pharmacol. 2005; 56 Suppl 1:47-57.

Gyrd-Hansen M and Meier P. IAPs: from caspase inhibitors to modulators of NF-kappaB, inflammation and cancer. Nat Rev Cancer. 2010; 10(8):561-574.

Hao Y, Sekine K, Kawabata A, Nakamura H, Ishioka T, Ohata H, Katayama R, Hashimoto C, Zhang X, Noda T, Tsuruo T and Naito M. Apollon ubiquitinates SMAC and caspase-9, and has an essential cytoprotection function. Nat Cell Biol. 2004; 6(9):849-860.

Hensley P, Mishra M and Kyprianou N. Targeting caspases in cancer therapeutics. Biol Chem. 2013; 394(7):831-843.

Houghton P J, Kang M H, Reynolds C P, Morton C L, Kolb E A, Gorlick R, Keir S T, Carol H, Lock R, Maris J M, Billups C A and Smith M A. Initial testing (stage 1) of LCL161, a SMAC mimetic, by the Pediatric Preclinical Testing Program. Pediatr Blood Cancer. 2012; 58(4):636-639.

Huo J, Xu S, Guo K, Zeng Q and Lam K P. Genetic deletion of faim reveals its role in modulating c-FLIP expression during CD95-mediated apoptosis of lymphocytes and hepatocytes. Cell Death Differ. 2009; 16(7):1062-1070.

Krajewska M, Krajewski S, Banares S, Huang X, Turner B, Bubendorf L, Kallioniemi O P, Shabaik A, Vitiello A, Peehl D, Gao G J and Reed J C. Elevated expression of inhibitor of apoptosis proteins in prostate cancer. Clin Cancer Res. 2003; 9(13):4914-4925.

Krieg A, Correa R G, Garrison J B, Le Negrate G, Welsh K, Huang Z, Knoefel W T and Reed J C. XIAP mediates NOD signaling via interaction with RIP2. Proc Natl Acad Sci USA. 2009; 106(34):14524-14529.

LaCasse E C, Mahoney D J, Cheung H H, Plenchette S, Baird S and Korneluk R G. IAP-targeted therapies for cancer. Oncogene. 2008; 27(48):6252-6275.

Lamers F, Schild L, Koster J, Speleman F, Ora I, Westerhout E M, van Sluis P, Versteeg R, Caron H N and Molenaar J J. Identification of BIRC6 as a novel intervention target for neuroblastoma therapy. BMC Cancer. 2012; 12:285.

Li F, Ackermann E J, Bennett C F, Rothermel A L, Plescia J, Tognin S, Villa A, Marchisio P C and Altieri D C. Pleiotropic cell-division defects and apoptosis induced by interference with survivin function. Nat Cell Biol. 1999; 1(8):461-466.

Lin D, Gout P W and Wang Y. Lessons from in-vivo models of castration-resistant prostate cancer. Curr Opin Urol. 2013; 23(3):214-219.

Lin D, Wyatt A W, Xue H, Wang Y, Dong X, Haegert A, Wu R, Brahmbhatt S, Mo F, Jong L, Bell R H, Anderson S, Hurtado-Coll A, Fazli L, Sharma M, Beltran H, et al. High fidelity patient-derived xenografts for accelerating prostate cancer discovery and drug development. Cancer Res. 2014; 74(4):1272-1283

Low C G, Luk I S, Lin D, Fazli L, Yang K, Xu Y, Gleave M, Gout P W and Wang Y. BIRC6 protein, an inhibitor of apoptosis: role in survival of human prostate cancer cells. PLoS One. 2013; 8(2):e55837.

Lu J, McEachern D, Sun H, Bai L, Peng Y, Qiu S, Miller R, Liao J, Yi H, Liu M, Bellail A, Hao C, Sun S Y, Ting A T and Wang S. Therapeutic potential and molecular mechanism of a novel, potent, nonpeptide, Smac mimetic SM-164 in combination with TRAIL for cancer treatment. Mol Cancer Ther. 2011; 10(5):902-914.

Martin S J. An Apollon vista of death and destruction. Nat Cell Biol. 2004; 6(9):804-806.

McManus D C, Lefebvre C A, Cherton-Horvat G, St-Jean M, Kandimalla E R, Agrawal S, Morris S J, Durkin J P and Lacasse E C. Loss of XIAP protein expression by RNAi and antisense approaches sensitizes cancer cells to functionally diverse chemotherapeutics. Oncogene. 2004; 23(49):8105-8117.

Mehrotra S, Languino L R, Raskett C M, Mercurio A M, Dohi T and Altieri D C. IAP regulation of metastasis. Cancer Cell. 2010; 17(1):53-64.

Pan W H, Clawson G A. Identifying accessible sites in RNA: the first step in designing antisense reagents. Curr Med Chem. 2006; 13(25):3083-103.

Patzel V. In silico selection of active siRNA. Drug Discov Today. 2007 February; 12(3-4):139-48.

Peek A S, Behlke M A. Design of active small interfering RNAs. Curr Opin Mol Ther. 2007 April; 9(2):110-8.

Petrylak D P, Tangen C M, Hussain M H, Lara P N, Jr., Jones J A, Taplin M E, Burch P A, Berry D, Moinpour C, Kohli M, Benson M C, Small E J, Raghavan D and Crawford E D. Docetaxel and estramustine compared with mitoxantrone and prednisone for advanced refractory prostate cancer. N Engl J Med. 2004; 351(15):1513-1520.

Pohl C and Jentsch S. Final stages of cytokinesis and midbody ring formation are controlled by BRUCE. Cell. 2008; 132(5):832-845.

Qiu X B, Markant S L, Yuan J and Goldberg A L. Nrdp1-mediated degradation of the gigantic IAP, BRUCE, is a novel pathway for triggering apoptosis. EMBO J. 2004; 23(4):800-810.

Qiu X B and Goldberg A L. The membrane-associated inhibitor of apoptosis protein, BRUCE/Apollon, antagonizes both the precursor and mature forms of Smac and caspase-9. J Biol Chem. 2005; 280(1):174-182.

Ren J, Shi M, Liu R, Yang Q H, Johnson T, Skarnes W C and Du C. The Birch (Bruce) gene regulates p53 and the mitochondrial pathway of apoptosis and is essential for mouse embryonic development. Proc Natl Acad Sci USA. 2005; 102(3):565-570.

Roca H, Varsos Z S and Pienta K J. CCL2 is a negative regulator of AMP-activated protein kinase to sustain mTOR complex-1 activation, survivin expression, and cell survival in human prostate cancer PC3 cells. Neoplasia. 2009; 11(12):1309-1317.

Rodriguez L, Villalobos X, Dakhel S, Padilla L, Hervas R, Hernandez J L, Ciudad C J and Noe V. Polypurine reverse Hoogsteen hairpins as a gene therapy tool against survivin in human prostate cancer PC3 cells in vitro and in vivo. Biochem Pharmacol. 2013; 86(11):1541-1554.

Sekine K, Hao Y, Suzuki Y, Takahashi R, Tsuruo T and Naito M. HtrA2 cleaves Apollon and induces cell death by IAP-binding motif in Apollon-deficient cells. Biochem Biophys Res Commun. 2005; 330(1):279-285.

Siegel R, Naishadham D and Jemal A. Cancer statistics, 2012. CA Cancer J Clin. 2012; 62(1):10-29.

Sung K W, Choi J, Hwang Y K, Lee S J, Kim H J, Lee S H, Yoo K H, Jung H L and Koo H H. Overexpression of Apollon, an antiapoptotic protein, is associated with poor prognosis in childhood de novo acute myeloid leukemia. Clin Cancer Res. 2007; 13(17):5109-5114.

Tamm I, Wang Y, Sausville E, Scudiero D A, Vigna N, Oltersdorf T and Reed J C. IAP-family protein survivin inhibits caspase activity and apoptosis induced by Fas (CD95), Bax, caspases, and anticancer drugs. Cancer Res. 1998; 58(23):5315-5320.

Tannock I F, de Wit R, Berry W R, Horti J, Pluzanska A, Chi K N, Oudard S, Theodore C, James N D, Turesson I, Rosenthal M A and Eisenberger M A. Docetaxel plus prednisone or mitoxantrone plus prednisone for advanced prostate cancer. N Engl J Med. 2004; 351(15):1502-1512.

Tassi E, Zanon M, Vegetti C, Molla A, Bersani I, Perotti V, Pennati M, Zaffaroni N, Milella M, Ferrone S, Carlo-Stella C, Gianni A M, Mortarini R and Anichini A. Role of Apollon in human melanoma resistance to antitumor agents that activate the intrinsic or the extrinsic apoptosis pathways. Clin Cancer Res. 2012; 18(12):3316-3327.

Thomas C, Zoubeidi A, Kuruma H, Fazli L, Lamoureux F, Beraldi E, Monia B P, MacLeod A R, Thuroff J W and Gleave M E. Transcription factor Stat5 knockdown enhances androgen receptor degradation and delays castration-resistant prostate cancer progression in vivo. Molecular cancer therapeutics. 2011; 10(2):347-359.

Tigno-Aranjuez J T, Bai X and Abbott D W. A discrete ubiquitin-mediated network regulates the strength of NOD2 signaling. Mol Cell Biol. 2013; 33(1):146-158.

Varfolomeev E, Goncharov T, Fedorova A V, Dynek J N, Zobel K, Deshayes K, Fairbrother W J and Vucic D. c-IAP1 and c-IAP2 are critical mediators of tumor necrosis factor alpha (TNFalpha)-induced NF-kappaB activation. J Biol Chem. 2008; 283(36):24295-24299.

Walia G, Pienta K J, Simons J W and Soule H R. The 19th annual prostate cancer foundation scientific retreat. Cancer Res. 2013; 73(16):4988-4991.

Yang C and Novack D V. Anti-cancer IAP antagonists promote bone metastasis: a cautionary tale. J Bone Miner Metab. 2013.

Zhao J, Tenev T, Martins L M, Downward J and Lemoine N R. The ubiquitin-proteasome pathway regulates survivin degradation in a cell cycle-dependent manner. J Cell Sci. 2000; 113 Pt 23:4363-4371.

Zielinski R, Eigl B J and Chi K N. Targeting the apoptosis pathway in prostate cancer. Cancer J. 2013; 19(1):79-89.

INFORMAL SEQUENCE LISTING

Description: dASO 6w2  
SEQ ID NO: 1  
5' CTGCAGCATC ATGTGGACT '3

Description: dASO 6w5  
SEQ ID NO: 2  
5' CAGGTGAAACACTGGGACA 3'

Description: Scramble (Scrb) B control (Non-targeting control ASO)  
SEQ ID NO: 3  
5' CCTTCCCTGAAGGTTCCTCC 3'

Description: mismatched (MM) control (Non-targeting control ASO)  
SEQ ID NO: 4  
5' CAGCAGCAGAGTATTTATCAT 3'

Description: dASO 6w4  
SEQ ID NO: 5  
5' ATCTGCCTCCAGAGTAGAC 3'

What is claimed is:

1. A method of treating cancer, the method comprising administering to a subject a dual-targeting antisense oligonucleotide (dASO) consisting of SEQ ID NO:1 or SEQ ID NO:2.

2. The method of claim 1, wherein the dASO comprises a modified internucleoside linkage.

3. The method of claim 2, wherein the modified internucleoside linkage is a peptide-nucleic acid linkage, a morpholino linkage, a N3' to P5' phosphoramidate linkage, a methylphosphonate linkage or a phosphorothioate linkage.

4. The method of claim 1, wherein the dASO comprises a modified sugar moiety.

5. The method of claim 4, wherein the modified sugar moiety is 2'-O-alkyl oligoribonucleotide.

6. The method of claim 1, wherein the dASO has a 2'MOE gapmer modification.

7. The method of claim 1, wherein the dASO comprises a modified nucleobase.

8. The method of claim 7, wherein the modified nucleobase is a 5-methyl pyrimidine or a 5-propynyl pyrimidine.

9. The method of claim 1, wherein the subject is human.

10. The method of claim 1, wherein the cancer is characterized by elevated expression of one of more of BIRC6 and cIAP1 or survivin.

11. The method of claim 10, wherein the cancer is selected from one or more of the following: prostate cancer; childhood de novo acute myeloid leukemia; colorectal cancer; neuroblastoma; melanoma; and non-small cell lung cancer.

12. The method of claim 11, wherein the cancer is castration-resistant prostate cancer (CRPC).

13. The method of claim 12, wherein the cancer is enzalutamide (ENZ) resistant CRPC.

14. The method of claim 1, wherein the dASO is administered intravenously.

15. The method of claim 1, wherein the dASO is topically administered to a tissue.

16. The method of claim 1, wherein the dASO is mixed with lipid particles prior to administration.

17. The method of claim 1, wherein the dASO is encapsulated in liposomes prior to administration.

18. A dual-targeting antisense oligonucleotide (dASO), wherein the oligonucleotide consists of a sequence selected from the following:

(a)
                               (SEQ ID NO: 1)
CTGCAGCATC ATGTGGACT;
and (b)
                               (SEQ ID NO: 2)
CAGGTGAAAC ACTGGGACA, wherein the dASO comprises a modification selected from a modified internucleoside linkage, a modified sugar moiety, a 2'MOE gapmer modification and a modified nucleobase.

19. The dASO of claim 18, wherein the dASO comprises a modified internucleoside linkage.

20. The dASO of claim 19, wherein the modified internucleoside linkage is a peptide-nucleic acid linkage, a morpholino linkage, a N3' to P5' phosphoramidate linkage, a methylphosphonate linkage or a phosphorothioate linkage.

21. The dASO of claim 18, wherein the dASO comprises a modified sugar moiety.

22. The dASO of claim 21, wherein the modified sugar moiety is 2'-O-alkyl oligoribonucleotide.

23. The dASO of claim 18, wherein the dASO has a 2'MOE gapmer modification.

24. The dASO of claim 18, wherein the dASO comprises a modified nucleobase.

25. The dASO of claim 24, wherein the modified nucleobase is a 5-methyl pyrimidine or a 5-propynyl pyrimidine.

26. A pharmaceutical composition, the composition comprising (a) dual-targeting antisense oligonucleotide (dASO) consisting of SEQ ID NO:1 or SEQ ID NO:2 wherein the dASO comprises a modification selected from a modified internucleoside linkage, a modified sugar moiety, a 2'MOE gapmer modification and a modified nucleobase; and (b) a pharmaceutically acceptable carrier.

27. The pharmaceutical composition of claim 26, wherein the dASO comprises a modified internucleoside linkage.

28. The pharmaceutical composition of claim 27, wherein the modified internucleoside linkage is a peptide-nucleic acid linkage, a morpholino linkage, a N3' to P5' phosphoramidate linkage, a methylphosphonate linkage or a phosphorothioate linkage.

29. The pharmaceutical composition of claim 26, wherein the dASO comprises a modified sugar moiety.

30. The pharmaceutical composition of claim 28, wherein the dASO comprises a modified sugar moiety.

31. The pharmaceutical composition of claim 30, wherein the modified sugar moiety is 2'-O-alkyl oligoribonucleotide.

32. The pharmaceutical composition of claim 26, wherein the dASO has a 2'MOE gapmer modification.

33. The pharmaceutical composition of claim 26, wherein the dASO comprises a modified nucleobase.

34. The pharmaceutical composition of claim 33, wherein the modified nucleobase is a 5-methyl pyrimidine or a 5-propynyl pyrimidine.

35. A commercial package, comprising: a. a dASO consisting of SEQ ID NO:1 or SEQ ID NO:2, wherein the dASO comprises a modification selected from a modified internucleoside linkage, a modified sugar moiety, a 2'MOE gapmer modification and a modified nucleobase; and b. instructions for the treatment of cancer.

36. The commercial package of claim 35, wherein the cancer is selected from one or more of the following: prostate cancer; childhood de novo acute myeloid leukemia; colorectal cancer; neuroblastoma; melanoma; and non-small cell lung cancer.

37. The commercial package of claim 35, wherein the prostate cancer is castration-resistant prostate cancer (CRPC).

* * * * *

SEQUENCE LISTING

<160> NUMBER OF SEQ ID NOS: 5

<210> SEQ ID NO 1
<211> LENGTH: 19
<212> TYPE: DNA
<213> ORGANISM: artificial sequence
<220> FEATURE:
<223> OTHER INFORMATION: dual targeting antisense oligonucleotide (dASO) 6w2

<400> SEQUENCE: 1
ctgcagcatc atgtggact                                              19

<210> SEQ ID NO 2
<211> LENGTH: 19
<212> TYPE: DNA
<213> ORGANISM: artificial sequence
<220> FEATURE:
<223> OTHER INFORMATION: dual targeting antisense oligonucleotide (dASO) 6w5

<400> SEQUENCE: 2
caggtgaaac actgggaca                                              19

<210> SEQ ID NO 3
<211> LENGTH: 20
<212> TYPE: DNA
<213> ORGANISM: artificial sequence
<220> FEATURE:
<223> OTHER INFORMATION: Scramble (Scrb) B control (non-targeting control ASO)

<400> SEQUENCE: 3
ccttccctga aggttcctcc                                             20

<210> SEQ ID NO 4
<211> LENGTH: 21
<212> TYPE: DNA
<213> ORGANISM: artificial sequence
<220> FEATURE:
<223> OTHER INFORMATION: Mismatched (MM) control (non-targeting control ASO)

<400> SEQUENCE: 4
cagcagcaga gtatttatca t                                           21

<210> SEQ ID NO 5
<211> LENGTH: 19
<212> TYPE: DNA
<213> ORGANISM: artificial sequence
<220> FEATURE:
<223> OTHER INFORMATION: dual targeting antisense oligonucleotide (dASO)

6w4

<400> SEQUENCE: 5
atctgcctcc agagtagac                                                                19